(12) United States Patent
Canary et al.

(10) Patent No.: US 7,943,751 B2
(45) Date of Patent: *May 17, 2011

(54) LADDER COPOLYMERS

(75) Inventors: James Wayne Canary, New York, NY (US); Nadrian C. Seeman, New York, NY (US); Lei Zhu, Austin, TX (US); Philip Lukeman, New York, NY (US)

(73) Assignee: New York University, New York, NY (US)

( * ) Notice: Subject to any disclaimer, the term of this patent is extended or adjusted under 35 U.S.C. 154(b) by 67 days.

This patent is subject to a terminal disclaimer.

(21) Appl. No.: 12/330,250

(22) Filed: Dec. 8, 2008

(65) Prior Publication Data

US 2009/0137738 A1  May 28, 2009

Related U.S. Application Data

(62) Division of application No. 10/855,893, filed on May 28, 2004, now Pat. No. 7,479,548.

(60) Provisional application No. 60/473,915, filed on May 29, 2003.

(51) Int. Cl.
*C07H 21/04* (2006.01)
*C07H 21/00* (2006.01)
*C07K 2/00* (2006.01)

(52) U.S. Cl. ............ 536/23.1; 536/25.3; 536/24.3; 530/300

(58) Field of Classification Search .............. None
See application file for complete search history.

(56) References Cited

OTHER PUBLICATIONS

Opalinska et al., *Nature Reviews Drug Discovery*, 1:503-514 (2002).

*Primary Examiner* — Tracy Vivlemore
(74) *Attorney, Agent, or Firm* — Browdy and Neimark, PLLC

(57) ABSTRACT

The present invention relates to a copolymer termed a ladder copolymer because it has two backbones that serve as legs/sides of a ladder structure. These two backbones, one of which is a nucleic acid or nucleic acid-like polymer, are linked together as the legs/sides of a ladder are linked together by the rungs.

15 Claims, 12 Drawing Sheets

SEQUENCE LISTING

<160> NUMBER OF SEQ ID NOS: 5

<210> SEQ ID NO 1
<211> LENGTH: 16
<212> TYPE: DNA
<213> ORGANISM: Artificial

-continued

```
<220> FEATURE:
<223> OTHER INFORMATION: synthetic
<220> FEATURE:
<221> NAME/KEY: misc_feature
<222> LOCATION: (7)..(7)
<223> OTHER INFORMATION: n is 2'-S- amino modified U.
<220> FEATURE:
<221> NAME/KEY: misc_feature
<222> LOCATION: (8)..(8)
<223> OTHER INFORMATION: n is 2'-S- carboxylmodified U.

<400> SEQUENCE: 1 tttttttnntt tttttt                                                  16

<210> SEQ ID NO 2
<211> LENGTH: 16
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (4)..(4)
<223> OTHER INFORMATION: n is 2'-S- amino modified U.
<220> FEATURE:
<221> NAME/KEY: misc_feature
<222> LOCATION: (5)..(5)
<223> OTHER INFORMATION: n is 2'-S- carboxylmodified U.
<220> FEATURE:
<221> NAME/KEY: misc_feature
<222> LOCATION: (8)..(8)
<223> OTHER INFORMATION: n is 2'-S- amino modified U.
<220> FEATURE:
<221> NAME/KEY: misc_feature
<222> LOCATION: (9)..(9)
<223> OTHER INFORMATION: n is 2'-S- carboxylmodified U.
<220> FEATURE:
<221> NAME/KEY: misc_feature
<222> LOCATION: (12)..(12)
<223> OTHER INFORMATION: n is 2'-S- amino modified U.
<220> FEATURE:
<221> NAME/KEY: misc_feature
<222> LOCATION: (13)..(13)
<223> OTHER INFORMATION: n is 2'-S- carboxylmodified U.

<400> SEQUENCE: 2
tttnnttnnt tnnttt                                                   16

<210> SEQ ID NO 3
<211> LENGTH: 16
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (8)..(8)
<223> OTHER INFORMATION: n is 2'-S- amino modified U.
<220> FEATURE:
<221> NAME/KEY: misc_feature
<222> LOCATION: (9)..(9)
<223> OTHER INFORMATION: n is 2'-S- carboxylmodified U.
<220> FEATURE:
<221> NAME/KEY: misc_feature
<222> LOCATION: (10)..(10)
<223> OTHER INFORMATION: n is 2'-S- amino modified U.
```

```
<400> SEQUENCE: 3
tttttttnnn tttttt                                                    16

<210> SEQ ID NO 4
<211> LENGTH: 16
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (8)..(8)
<223> OTHER INFORMATION: n is 2'-S- carboxylmodified U.
<220> FEATURE:
<221> NAME/KEY: misc_feature
<222> LOCATION: (9)..(9)
<223> OTHER INFORMATION: n is 2'-S- amino modified U.
<220> FEATURE:
<221> NAME/KEY: misc_feature
<222> LOCATION: (10)..(10)
<223> OTHER INFORMATION: n is 2'-S- carboxylmodified U.

<400> SEQUENCE: 4
tttttttnnn tttttt                                                    16

<210> SEQ ID NO 5
<211> LENGTH: 16
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (7)..(7)
<223> OTHER INFORMATION: n is 2'-S- carboxylmodified U.
<220> FEATURE:
<221> NAME/KEY: misc_feature
<222> LOCATION: (8)..(8)
<223> OTHER INFORMATION: n is 2'-S- amino modified U.
<220> FEATURE:
<221> NAME/KEY: misc_feature
<222> LOCATION: (9)..(9)
<223> OTHER INFORMATION: n is 2'-S- carboxylmodified U.
<220> FEATURE:
<221> NAME/KEY: misc_feature
<222> LOCATION: (10)..(10)
<223> OTHER INFORMATION: n is 2'-S- amino modified U.

<400> SEQUENCE: 5 tttttttnnnn tttttt                                                   16
```

LADDER COPOLYMERS

CROSS REFERENCED WITH RELATED APPLICATIONS

The present application is a division of application Ser. No. 10/855,893, filed May 28, 2004, and now issued as U.S. Pat. No. 7,479,548, which claims priority from provisional application 60/473,915, filed May 29, 2003, the entire content of these applications are hereby incorporated by reference.

GOVERNMENT LICENSE RIGHTS

The experiments performed in this application were supported in part by the Office of Naval Research, grant no. N00014-98-1-0093, by the National Institutes of Health, grant no. GM-29554, by the National Science Foundation, grant nos. CHE-0079702, DMI-0210844, EIA-0086015, DMR-01138790, and CTS-0103002, and by DARPA/AFSOR grant no. F30602-01-2-0561. The U.S. Government has a paid-up license in this invention and the right in limited circumstances to require the patent owner to license others on reasonable terms as provided for by the terms of the above grants.

BACKGROUND OF THE INVENTION

1. Field of the Invention

The present invention relates to ladder copolymers in which one of two backbones (legs or sides of a ladder) is formed of a nucleic acid or nucleic acid-like polymer.

2. Description of the Related Art

During the past half-century the known functions of nucleic acids have expanded from genetic information carriers and messengers to include catalysis and regulation of a number of cellular processes. In addition, many nucleic acid-based structures have been developed with medicinal applications, catalytic properties, and prebiotic chemistry implications (Pearson, 2003; Dennis, 2002; Couzin, 2002). Notable examples are antisense agents (Uhlmann et al., 1990), e.g., peptide nucleic acid (PNA) (Nielsen, 1999), deoxynucleic guanidine (DNG) (Barawkar et al., 1999), and locked DNA (LNA) (Vester et al., 2002; Demidov, 2003). DNAzymes have been developed with functionalized nucleotidyl groups to enhance catalytic abilities (Santoro et al., 2000; Thum et al., 2001; Lermer et al., 2002). TNA, (3',2')-α-L-threose nucleic acid, has been suggested as an evolutionary progenitor of RNA and/or DNA (Schöning et al., 2000; Chaput et al., 2003).

A goal of the present inventors is to develop new nucleic acid-based materials to expand the applications and scope of DNA nanotechnology (Seeman, 1999). A number of topological targets, objects, devices, and 2D arrays have been prepared from conventional DNA molecules with defined sequences and unusual structural motifs (Seeman, 2003; U.S. Pat. Nos. 5,386,020; 6,072,044; 6,255,469). Analogous DNA/organic polymer conjugates of these structures offer practical interest. For example, DNA 2D arrays (Winfree et al., 1998) may serve as platforms to assemble molecular electronic devices with nanometer precision, or as templates to synthesize non-DNA polymeric 2D networks that would enjoy the stability and other favorable properties of organic materials. Single-stranded DNA has been used to direct polymerization of DNA oligos with unnatural linkages (Li et al., 2002; Schmidt et al., 1997; Seitz et al., 2001). An object of the present invention is to harness the full power of DNA nanotechnology, which depends on both secondary and tertiary DNA structural motifs, to assemble organic materials with unique structures, and the approach of the present inventors also entails regio-specific chemistry between non-DNA entities.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a ladder copolymer having two backbones as the sides or legs of a ladder with links between the backbones serving as rungs of the ladder. One of the two backbones is a nucleic acid or nucleic acid-like backbone. The ladder copolymer has a structure that includes the general formula (I)

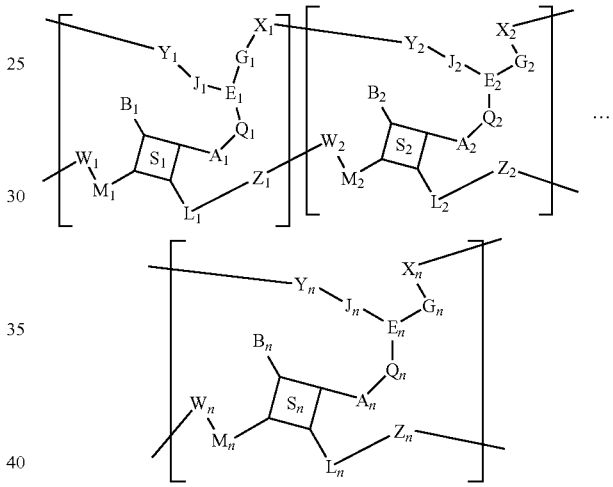

where:

A=a Group VI element selected from the group consisting of O, S, Se, and Te;

G, J, L, M, Q=a linker group selected from the group consisting of $C_1$-$C_{18}$ branched or straight chain alkyl groups, $C_6$-$C_{24}$ substituted or unsubstituted aromatic and heteroaromatic groups having from 1-3 hetero atoms (N, S, O) or halogen substitutions, —O—, —S—, carbonyl, carboxyl, —$SiR_2$—, and —$OSiR_2O$—;

B=a nucleic acid base selected from the group consisting of U, T, A, G, C, and a derivative thereof;

E=a symmetric or asymmetric atom center selected from the group consisting of CR, N, NR+, phosphine, phosphine oxide, phosphate, phosphonate, phosphinate, phosphoramide, phosphonamide, and phosphinamide;

R=a terminal group selected from the group consisting of H, $C_1$-$C_{18}$ branched or straight chain alkyl groups, $C_6$-$C_{24}$ substituted or unsubstituted aromatic and heteroaromatic groups having from 1-3 hetero atoms (N, S, O) or halogen substitutions;

Pairs X—Y, W—Z=bonding sites such that X can be caused to form a chemical bond with Y, or W with Z, by the techniques of organic synthesis; and S=a ribose or any modified ribose or similar cyclic or acyclic building block associated with a DNA-like structure.

The present invention further provides a method of producing the ladder copolymer and a method for inhibiting the production of a polypeptide or peptide encoded by a mRNA by using the ladder copolymer as a stable antisense molecule.

DETAILED DESCRIPTION OF THE INVENTION

Figure 1:
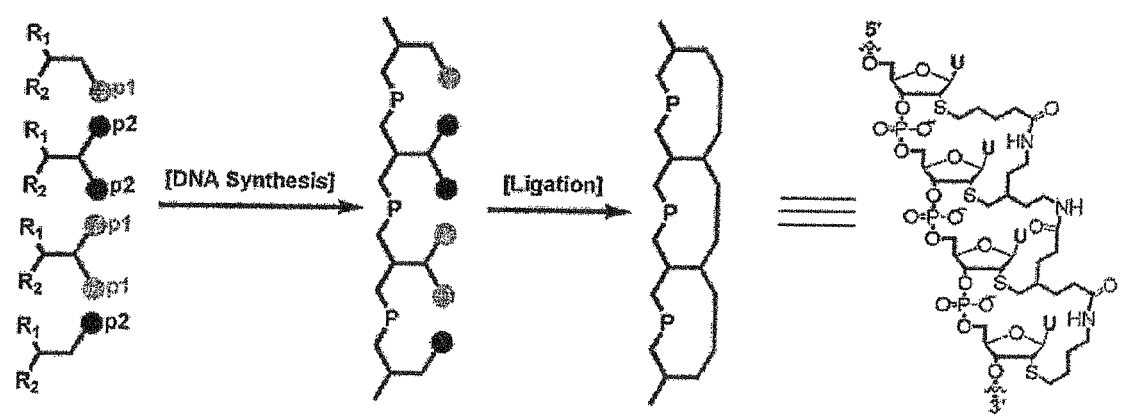
FIG. 1 shows a schematic illustration of a ladder oligomer/copolymer synthesis from modified phosphoramidites to uncoupled strands and then ligation to form the ladder oligomer/copolymer. $R_1$: -DMTr; $R_2$: —P(NiPr$_2$)(OCH$_2$CH$_2$CN); gray and black dots are carboxyl and amino groups respectively; p1 and p2 are their respective protecting groups. Vertical chains with alternate "P" represent a nucleic acid backbone; the vertical chain opposite the nucleic acid backbone represents the nylon backbone; the horizontal lines (right) represent "rungs" on the ladder oligomer/copolymer. The structure on the far right shows a ladder copolymer constructed in the Examples presented below.

The present invention is directed to a copolymer which is termed a ladder copolymer because it has two different backbone polymers that serve as legs/sides of a ladder structure. These two backbones, one of which is a nucleic acid or a nucleic acid-like polymer, are linked together as the legs/sides of a ladder are linked together by the rungs of the ladder.

The term "nucleic acid" refers to both DNA and RNA and hybrids of the two. Furthermore, the nucleic acid backbone structure need not resemble anything which can theoretically be made from nature.

A generic structure of the ladder copolymer of the present invention is presented below as general formula (I).

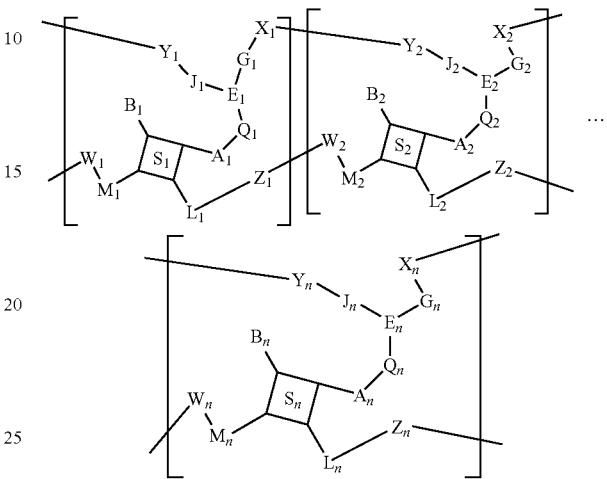

wherein:
A=a Group VI element selected from the group consisting of O, S, Se, and Te;

G, J, L, M, Q=a linker group selected from the group consisting of C$_1$-C$_{18}$ branched or straight chain alkyl groups, C$_6$-C$_{24}$ substituted or unsubstituted aromatic and heteroaromatic groups having from 1-3 hetero atoms (N, S, O) or halogen substitutions, —O—, —S—, carbonyl, carboxyl, —SiR$_2$—, and —OSiR$_2$O—;

B=a nucleic acid base selected from the group consisting of U, T, A, G, C, and a derivative thereof;

E=a symmetric or asymmetric atom center selected from the group consisting of CR, N, NR+, phosphine, phosphine oxide, phosphate, phosphonate, phosphinate, phosphoramide, phosphonamide, and phosphinamide;

R=a terminal group selected from the group consisting of H, C$_1$-C$_{18}$ branched or straight chain alkyl groups, C$_6$-C$_{24}$ substituted or unsubstituted aromatic and heteroaromatic groups having from 1-3 hetero atoms (N, S, O) or halogen substitutions;

Pairs X—Y, W—Z=bonding sites such that X can be caused to form a chemical bond with Y, or W with Z, by the techniques of organic synthesis; and S=a ribose or any modified ribose or similar cyclic or acyclic building block associated with a DNA-like structure.

The subscripts, e.g., 1, 2, n, etc., denote not only a sequence in the chain of units (brackets) forming a copolymer but also denote that the moieties designated by the letters, e.g., B, W, Z, X, Y, etc., may or may not be the same from unit to unit.

Pairs X—Y and W—Z preferably form amide, ester, phosphoester, or alkene bonds, such as from electrocyclic reactions. Although pairs X—Y and W—Z may have the same bonds, they are preferably different bonds. Most preferably, the X—Y pair forms an amide bond, and the W—Z pair forms a phosphoester bond that is present in a nucleic acid backbone, as will be apparent from the preferred embodiments described below.

The nucleic acid backbone need not have a single contiguous ribose-phosphate or deoxyribose-phosphate backbone.

One may employ a simple inorganic or organic moiety or polymeric spacer between segments of polynucleotide. Spacers such as polyethylene, polyvinyl polymers, polypropylene, polyethylene, polyvinyl polymers, polypropylene, polyethylene glycol, polystyrene, polypeptides (enzymes, antibodies, etc.) peptide nucleic acids (PNA), polysaccharides (starches, cellulose, etc.) silicones, silanes and copolymers, etc., may be employed. An example of such a hybrid structure is dodecadiol having phosphoramidite at one end. This structure has been inserted covalently in place of four T nucleotides to form a hairpin loop in a fashion similar to the nucleotides it replaces. The term "oligonucleotide", "polynucleotide" and nucleic acid" are intended to cover all of these structures.

Furthermore, it should be appreciated that while the W—Z pair most preferably forms a phosphoester bond, there may also be locations along the nucleic acid backbone where a particular W—Z pair does not form a phosphoester bond. This non-uniformity, in which there is not a single contiguous ribose-phosphate or deoxyribose-phosphate backbone, leads to a backbone or polymer termed "nucleic acid-like". Some examples of such modified backbones which are "nucleic acid-like" are presented in the study of Freier et al. (1997), the entire contents of which are herein incorporated by reference.

The nucleic acid or nucleic acid-like polymer backbone strand may employ bases (B) other than the standard five, adenine (A), cytosine (C), guanine (G), thymine (T), and uracil (U). Derivatized/modified (e.g., methylated) and other unusual bases such as iso-guanine, iso-cytosine, amino-adenine, K, X, pi, inosine and other derivatives of purines and pyrimidines may be used. Some examples of derivatized/modified bases are presented in Freier et al. (1997). A preferable feature in the selection of the bases is that they be capable of interacting with a base opposing them to form a specifically paired attraction. In natural DNA and RNA, hydrogen bonding forms this interaction. However, opposite ion charges, hydrophobic interactions and van der Waals forces may also be acceptable forms of interaction. These interactions expand the choices over naturally occurring bases to give a wider assortment of physical properties.

Within a particular strand, the heterocyclic base may be entirely missing from the sugar moiety. This may be particularly desirable where the strands bend, form a junction, or where one desires fewer forces holding the strands together.

S represents a ribose or any modified ribose or similar cyclic or acyclic building block associated with a DNA-like structure (e.g., PNA and morpholino backbones). Non-limiting examples of ribose, modified ribose and similar building block units are presented below.

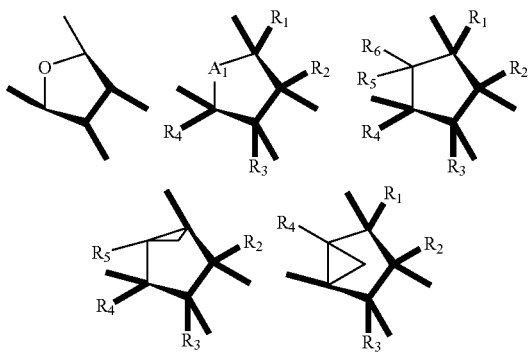

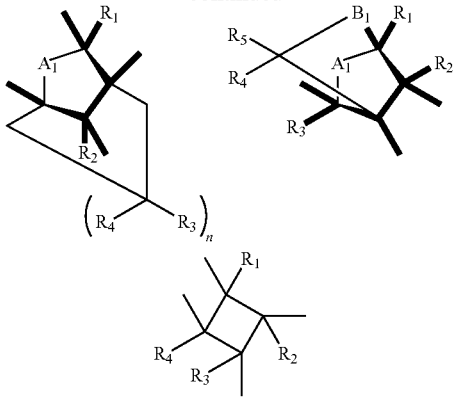

Additional non-limiting examples of modified ribose/sugar are presented in Freier et al. (1997).

The preference for uniformity of the W—Z bond in the nucleic acid backbone also applies for the X—Y bond. However, the present invention is also intended to encompass the presence of non-uniform X—Y bonds in the backbone opposite the nucleic acid or nucleic acid-like backbone. It should also be appreciated that the presence of side chains may be desirable on the opposing backbone with the X—Y pairings. For instance, if one wanted to attach gold particles to the opposing backbone, i.e., once per DNA turn, then a varied diamino or dicarboxyl group containing a sulfhydryl side chain, which is capable of forming a bond with a gold particle, can be inserted into the backbone at appropriate locations.

In one preferred embodiment of the ladder copolymer of the present invention, the opposing backbone, which is opposite the nucleic acid nucleic acid-like backbone, is a polyamide backbone and the ladder copolymer includes the general formula (II)

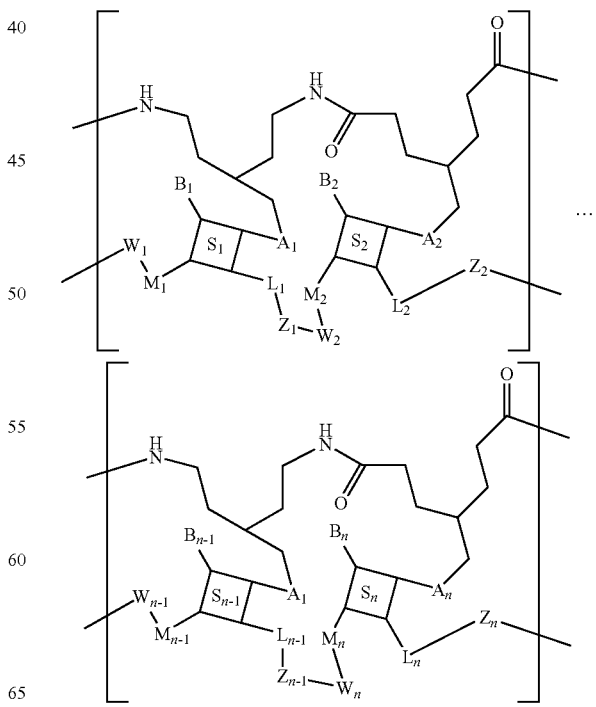

where:

A=a Group VI element selected from the group consisting of O, S, Se, and Te; and L, M=a linker group selected from the group consisting of $C_1$-$C_{18}$ branched or straight chain alkyl groups, $C_6$-$C_{24}$ substituted or unsubstituted aromatic and heteroaromatic groups having from 1-3 hetero atoms (N, S, O) or halogen substitutions, —O—, —S—, carbonyl, carboxyl, —$SiR_2$—, and —$OSiR_2O$—;

B=a nucleic acid base selected from the group consisting of U, T, A, G, C and a derivative thereof;

R=a terminal group selected from the group consisting of H, $C_1$-$C_{18}$ branched or straight chain alkyl groups, $C_6$-$C_{24}$ substituted or unsubstituted aromatic and heteroaromatic groups having from 1-3 hetero atoms (N, S, O) or halogen substitutions;

W—Z=bonding sites such that W can be caused to form a chemical bond with Z by the techniques of organic synthesis; and S=a ribose or any modified ribose or similar cyclic or acyclic building block associated with a DNA-like structure.

In a second preferred embodiment of the ladder copolymer of the present invention, one of the backbones is a nucleic acid backbone and the ladder copolymer includes the general formula (III)

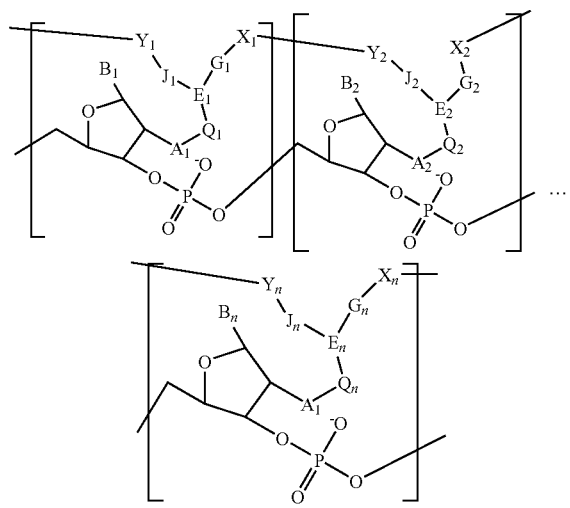

where:

A=a Group VI element selected from the group consisting of O, S, Se, and Te;

G, J, Q=a linker group selected from the group consisting of $C_1$-$C_{18}$ branched or straight chain alkyl groups, $C_6$-$C_{24}$ substituted or unsubstituted aromatic and heteroaromatic groups having from 1-3 hetero atoms (N, S, O) or halogen substitutions, —O—, —S—, carbonyl, carboxyl, —$SiR_2$—, and —$OSiR_2O$—;

B=a nucleic acid base selected from the group consisting of U, T, A, G, C and a derivative thereof;

E=a symmetric or asymmetric atom center selected from the group consisting of CR, N, NR+, phosphine, phosphine oxide, phosphate, phosphonate, phosphinate, phosphoramide, phosphonamide, and phosphinamide;

R=a terminal group selected from the group consisting of H, $C_1$-$C_{18}$ branched or straight chain alkyl groups, $C_6$-$C_{24}$ substituted or unsubstituted aromatic and heteroaromatic groups having from 1-3 hetero atoms (N, S, O) or halogen substitutions; and X—Y=bonding sites such that X can be caused to form a chemical bond with Y by the techniques of organic synthesis.

As another preferred embodiment of the ladder copolymer of the present invention, the two backbones are a nucleic acid backbone and a polyamide backbone. A most preferred embodiment includes the general formula (IV)

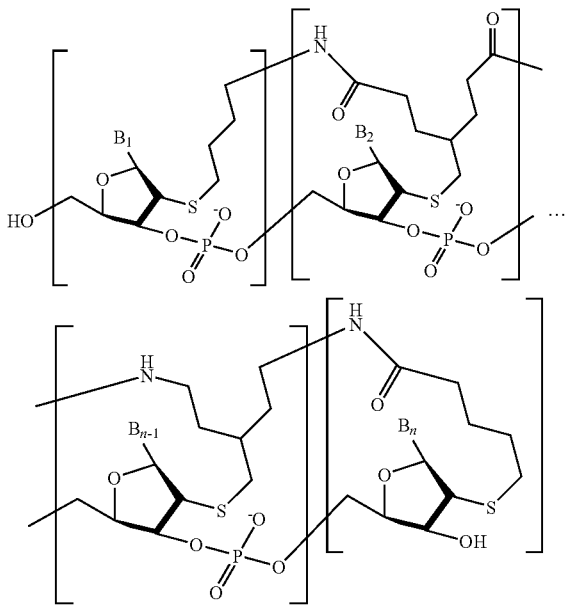

where B is a nucleic acid base selected from the group consisting of U, T, A, G, C, and derivatives thereof. Thus, the ladder copolymer of formula (IV) has a DNA backbone covalently linked to a polyamide backbone via the 2'-position of the ribose rings. Links (rungs of the ladder) are present for each nucleotide, and one amide bond is present per linked nucleotide. The polyamide backbone shown in formulas (III) and (IV) approximates the equivalent of Nylon-5,7. Other suitable polyamide or nylon backbones can be used in the ladder copolymer of the present invention. See for example, Kirk-Othmer *Encyclopedia of Chemical Technology*, 4$^{th}$ ed., editors J. I. Kroschwitz and M. Howe-Grant, John Wiley & Sons, New York, volume 19, pages 454-559 on polyamides (general) and polyamides in fibers, the entire contents of which are incorporated herein by reference.

The present invention is also directed to a method of forming/producing the ladder copolymer of the present invention having a DNA backbone. This method involves synthesizing 2'-β-substituted phosphoramidites, then synthesizing oligonucleotides with pendent groups from the synthesized 2'-β-substituted phosphoramidites, followed by coupling the pendent groups to produce a ladder copolymer. For formula (IV), the pendent groups that are coupled are amine and carboxylate groups. A scheme for producing the ladder copolymer is presented in FIG. 1.

It is expected that the ladder copolymer according to the present invention will confer stability to nuclease digestion while maintaining or enhancing the stability of duplex or triple strand formation with DNA or RNA. Moreover, it is also expected that a ladder copolymer with a nucleic acid backbone, if not also a ladder copolymer with a nucleic acid-like backbone, will form an A-form helix in combination with a single stranded DNA or RNA or with another ladder copolymer. The opposing backbone is further expected to be located on the outside of the helix, away from the pairing functions of the bases where it would not interfere with base pairing in double or triple strand formation. Accordingly, the ladder copolymer can serve to provide advantageous properties to antisense technology. For instance, the ladder copolymer can be designed with a base sequence that forms a stable duplex with a target sense mRNA to render the target normal or sense mRNA inactive and untranslatable. Therefore, the present invention also provides a method for inhibiting the production of a polypeptide or peptide encoded by a mRNA by bringing the ladder copolymer according to the present invention, which serves as an antisense oligomer, into contact with a target mRNA to which it anneals/hybridizes to form a stable duplex to inhibit the production of the encoded polypeptide or peptide.

Figures 2A, 2B, 2C, 2D:
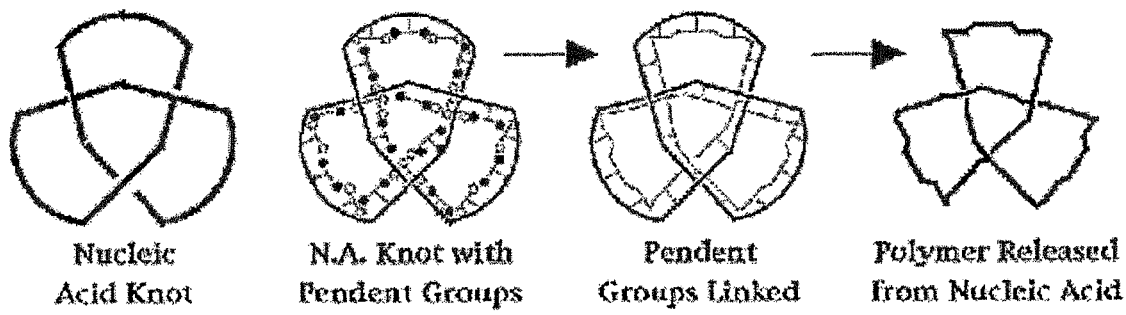
FIGS. 2A-2D show a nucleic acid knot (FIG. 2A) and a nucleic acid knot with pendent groups (FIG. 2B) which can be linked to form a ladder copolymer (FIG. 2C). The linkage of the pendent copolymer enables the polymer to retain the knot structure upon release from the nucleic acid (FIG. 2D).

The ladder copolymer can also be used to direct the production of desired polymers, i.e., industrial polymers, with a unique molecular topology (Gartner et al. 2002). A DNA knot (FIG. 2A) is a non-limiting example of a unique molecular topology (Mueller et al., 1991; Du et al., 1992; Seeman, 1992; Wang et al., 1993; Seeman et al., 1993; Du et al., 1994; Du et al., 1995). Were a DNA (knot) used to template the assembly of a ladder copolymer (FIGS. 2B and 2C) with a desired polymer i.e., nylon as an example of fiber polymers for which unique molecular topologies may be advantageous, the DNA could be removed, leaving the desired polymer in retention of the knot structure (FIG. 2D). Again, using nylon as an example, a nylon-based DNA chain mail-like structure can be formed by linking the nylon components pendent from the DNA. Removal of the DNA would lead to nylon chain mail, a molecular analog of iron chain mail which should exhibit remarkable strength.

Having now generally described the invention, the same will be more readily understood through reference to the following example which is provided by way of illustration and is not intended to be limiting of the present invention.

EXAMPLE

Here, the present inventors report the first nucleic acid-based structure in which a DNA backbone has been covalently linked to an organic polymer, nylon. The synthesis was accomplished in three stages: Preparation of 2'-β-substituted phosphoramidites, synthesis of oligonucleotides (ODNs) with appended amine and carboxylate groups, and coupling of the pendent groups to form oligoamide strands covalently linked at each nucleotide pair to give a nylon-DNA ladder copolymer (FIG. 1). The strategy is general and could be used to generate a variety of nylon-based materials, or to direct the assembly of other organic polymers.

Materials and Methods

All chemicals and solvents were of the required purity from various commercial sources. $CH_2Cl_2$ and $CH_3CN$ were dried by refluxing with $CaH_2$. All reactions were performed under argon gas protection; dehydration conditions were invoked when required. $^1$H NMR, $^{13}$C NMR, $^{31}$P NMR and $^1$H COSY data were recorded on Varian Gemini-200 or 300 MHz spectrometers. Matrix-assisted laser desorption ionization time-of-flight (MALDI-TOF) mass spectra in positive mode were measured with a Kratos MALDI-I spectrometer using the matrix α-cyano-4-hydroxycinnamic acid (CHCA). MALDI-TOF mass spectra in negative mode were measured with a Bruker OmniFLEX spectrometer using trihydroxyacetophenone (THAP) as matrix and ammonium tartrate as co-matrix. Compounds 2'-deoxy-2'-S-(4-methoxybenzyl)uridine (Divakar et al., 1982) and 1a (Zhu et al., 2002) were prepared by literature procedures. The synthesis of compounds 1a and 1b are provided below.

2-(2'-Phthaloylethyl)-4-phthaloyl-1-butene (B1)

A suspension of zinc dust (0.89 g, 13.7 mmol, 326 mesh) in THF (3.0 mL) and dibromomethane (0.2 mL) was heated to reflux for 15 min. Then trimethylsilylchloride (0.5-0.7 mL) was added to the mixture which was sonicated for 5 min. under argon. The solvent was eliminated under vacuum until dryness. To the activated zinc was added anhydrous DMSO (5.0 mL) under argon. N-Bromomethylphthalimide (3.0 g, 12.5 mmol) previously dissolved in THF (20 mL) was then added dropwise. The mixture was stirred for 2 h at room temperature and allowed to stand in order to precipitate the excess of zinc. The clear solution of organozinc compound was added dropwise via syringe to a solution of THF (40 mL), CuCN (0.9 g, 10 mmol), LiCl (1.0 g, 23.6 mmol) and 3-iodo-2-iodomethyl-propene[34] (2.5 mmol) at −60° C. The mixture was stirred vigorously at room temperature for 72 h and quenched with a saturated $NH_4Cl$ solution (150 mL). The organic layer was separated and the aqueous phase was extracted 3 times with ethyl ether. The organic layers were combined, dried over $MgSO_4$ and concentrated under vacuum. The crude product was chromatographed with silica gel initially using 9:1 hexanes/ethyl acetate, and then increasing the polarity to 8:2 hexanes/ethyl acetate to give 0.68 g (71%) of the product. $^1$H NMR (200 NMR, $CDCl_3$) δ 7.9-7.8 (m, 4H), 7.7-7.6 (m, 4H), 4.7 (s, 2H), 3.82 (t, 4H, J=7.0 Hz), 2.49 (t, 4H, J=7.0 Hz); $^{13}$C NMR (50 MHz, $CDCl_3$) δ 168.6, 142.7, 134.3, 132.6, 123.6, 115.0, 36.9, 34.7; MS (MALDI-TOF) calcd (M+H$^+$) 375.4, found 375.6; Anal. calcd for $C_{22}H_{18}N_2O_4$: C, 70.58; H, 4.85; N, 7.48. Found: C, 70.73; H, 4.65; N, 7.46; mp: 134-136° C.

2-(2'-Phthaloylethyl)-4-phthaloyl-butanol (B2)

A 1.0 M solution of $BH_3$ in THF (5.8 mL, 5.8 mmol) was added slowly to a solution of B1 (2.0 g, 5.3 mmol) in THF (50 mL) at 0° C. over 20 minutes. The mixture was stirred for additional 15 minutes at 0° C. and then quenched with 30% hydrogen peroxide (2.0 mL) which was added dropwise until the evolution of hydrogen stopped. The solution was made alkaline with 4-5 mL of a 30% NaOH and stirred for 15 minutes. To the mixture was added water (150 mL) and ethyl ether (150 mL). The organic layer was separated and the aqueous phase was extracted 3 times with ethyl ether. The organic layers were combined, dried over $MgSO_4$ and filtered. The solvent was removed under vacuum and the residue was chromatographed on silica gel (9:1 $CHCl_3$: ethyl ether) to give 1.18 g (57%) product. $^1$H NMR (200 MHz, $CDCl_3$) δ 7.8-7.7 (m, 8H), 3.79-3.70 (m, 6H), 2.3 (br, s, 1H), 1.8 (q, 4H, J=7.0 Hz), 1.55 (m, 1H); $^{13}$C NMR (50 MHz, $CDCl_3$) δ 168.8, 134.3, 132.6, 123.6, 65.7, 36.3, 36.2, 30.9; mp: 142-145° C.

2-(2'-Phthaloylethyl)-4-phthaloyl-1-iodo-butane (1a)

Compound B2 (39.0 mg, 0.1 mmol), triphenylphosphine (79.0 mg, 0.3 mmol), iodine (56.0 mg, 0.3 mmol) and imidazole (21.0 mg, 0.3 mmol) were dissolved in THF (1.0 mL). The solution was stirred at room temperature for 1 h while much white precipitate was formed. The solution was partitioned between $CH_2Cl_2$ and water. The organic layer was washed with water and dried over $Na_2SO_4$. After removing the solvent under vacuum, the residue was chromatographed with $CH_2Cl_2$/ethyl acetate (20/1 to 1/1) to give pure compound 1a (49.1 mg) in 98% yield. $^1$H NMR (200 MHz, CDCl$_3$) δ 7.8-7.7 (m, 8H), 3.7 (m, 4H), 3.4 (d, 2H, J=3.9 Hz), 1.7 (m, 4H), 1.1 (m, 1H); $^{13}$C NMR (50 MHz, CDCl$_3$) δ 168.7, 134.3, 132.5, 123.6, 35.6, 33.9, 33.8, 15.2; MS (FAB) calcd (M+H$^+$) 503.04, found 502.85; Anal. calcd for C$_{22}$H$_{19}$N$_2$O$_4$I: C, 52.60; H, 3.81; N, 5.57. Found: C, 52.46; H, 3.63; N, 5.58. mp: 168-172° C.

Dibenzyl-4-oxopimelate (B3)

γ-Ketopimelic acid (3.5 g, 20 mmol) was dissolved in anhydrous DMF (80 mL). DIEA (14 mL, 80 mmol) and benzylbromide (5.3 mL, 44 mmol) were added subsequently. The solution was heated at 80° C. for 20 h. After removing solvent under vacuum it was partitioned between Et$_2$O (200 mL) and water (100 mL). The organic layer was washed with water (2×50 mL) and dried over Na$_2$SO$_4$. The solvent was removed and dibenzyl-4-oxopimelate was recrystallized from Et$_2$O/petroleum ether with 94% yield. $^1$H NMR (200 MHz, CDCl$_3$) δ 7.37 (m, 10H), 5.11 (s, 4H), 2.78 (m, 4H), 2.68 (m, 4H); $^{13}$C NMR (50 MHz, CDCl$_3$) δ 207.1, 172.9, 136.3, 129.0, 128.72, 128.67, 67.1, 37.7, 28.6.

Dibenzyl-4-methyleneheptanedioate (B4)

Methyltriphenylphosphonium bromide (536 mg, 1.5 mmol) was suspended in anhydrous THF (1.0 mL) at −5C. A THF solution of NaHMDS (1.0 M, 1.5 mL, 1.5 mmol) was added dropwise to keep the temperature below 0° C. The mixture was stirred at 0° C. for 0.5 h before cooled to −78° C. To this ylid solution was added a solution of dibenzyl-4-oxopimelate (354 mg, 1.0 mmol) in THF (1.0 mL) dropwise to keep the temperature below −50° C. The temperature was allowed to rise to room temperature in 1.5 h with stirring after addition. The reaction mixture was then poured in icy water (25 mL) and extracted with Et$_2$O (2×25 mL). The organic layer was washed with brine (20 mL) and dried over Na$_2$SO$_4$. The solvent was removed under vacuum and the residue was subjected to silica chromatography (EtOAc/hexanes, up to 1/10) to give compound B4 (197 mg). The yield was 56%. $^1$H NMR (200 MHz, CDCl$_3$) δ 7.37 (m, 10H), 5.11 (s, 4H), 4.78 (d, 2H, J=1.1 Hz), 2.53 (m, 4H), 2.39 (m, 4H); $^{13}$C NMR (50 MHz, CDCl$_3$) δ 173.3, 146.6, 136.4, 129.0, 128.7, 110.5, 66.9, 33.2, 31.6; MS (MALDI-TOF) calcd (M+Na$^+$) 375.4, found 375.6.

Dibenzyl-4-(iodomethyl)heptanedioate (1b)

Compound B4 (176 mg, 0.5 mmol) was dissolved in anhydrous THF (0.5 mL). The solution was cooled to 0° C. and BH$_3$-THF (2.0 M, 0.25 mL, 0.5 mmol) was added via a syringe. The solution was then stirred at room temperature for 1 h. Methanolic NaOAc (3.0 mL, 1.0 M, 3.0 mmol), aqueous NaI (3.0 mL, 1.0 M, 3.0 mmol) and methanolic chloramine-T (6.0 mL, 0.5 M, 3.0 mmol) were added sequentially to the organoborane solution at room temperature. The reaction mixture were stirred for 10 min at room temperature and then quenched with aqueous Na$_2$S$_2$O$_3$ (1.0 M). The mixture was partitioned between Et$_2$O (50 mL) and H$_2$O (50 mL) and the organic layer was washed with brine (30 mL) before drying over Na$_2$SO$_4$. The solvent was evaporated and the residue was subjected to silica chromatography (CH$_2$Cl$_2$/hexanes, 2/100 to 7/100) to yield compound 1b (85 mg). The yield was 35%. $^1$H NMR (200 MHz, CDCl$_3$) δ 7.37 (m, 10H), 5.11 (s, 4H), 3.21 (d, 2H, J=8.0 Hz), 2.37 (m, 4H), 1.68 (m, 4H), 1.20 (m, 1H); $^{13}$C NMR (50 MHz, CDCl$_3$) δ 173.2, 136.3, 129.1, 128.8, 66.9, 37.5, 31.8, 29.9, 14.5; MS (MALDI-TOF) calcd (M+Na$^+$) 503.3, found 503.8.

2'-Deoxy-2'-S-(4-phthalimidylbutyl)uridine (Compound 2c)

A solution of 2'-deoxy-2'-S-(4-methoxybenzyl)uridine (1.14 g, 3.0 mmol) and phenol (423 mg, 4.5 mmol) in TFA (12.0 mL) was heated (bath temperature 100° C.) under reflux for 2 h. After cooling, the solvent was removed under reduced pressure. The residue was co-evaporated with CH$_3$CN (10 mL) 3 times before dissolving in Et$_2$O (2 mL). The crude 2'-deoxy-2'-mercaptouridine was precipitated by addition of hexanes (20 mL) and kept at −20° C. for 30 min. The solution was decanted and the residue was washed with hexanes (3×10 mL) before drying under vacuum (15 min). The crude 2'-deoxy-2'-mercaptouridine was dissolved in CH$_3$CN (3.0 mL) followed by addition of N-(4-bromobutyl)phthalimide (846 mg, 4.5 mmol). Diisopropyl ethylamine (DIEA) (2.6 mL, 15.0 mmol) was added dropwise into the reaction mixture with vigorous stirring. The solution was stirred at room temperature for 16 h before the solvent was removed under reduced pressure. The residue was dissolved in EtOAc (100 mL), washed twice with saturated aqueous NaHCO$_3$ (2×50 mL) and brine (30 mL) sequentially. The organic layer was dried over Na$_2$SO$_4$. The solvent was removed and the residue was subjected to silica chromatography (2% CH$_3$OH/CH$_2$Cl$_2$) to give 2c (1.18 g). The yield was 85%. $^1$H NMR (300 MHz, CD$_3$OD) δ 8.02 (d, 1H, J=8.2 Hz, 6-H), 7.89-7.77 (m, 4H), 6.09 (d, 1H, J=8.5 Hz, 1'-H), 5.70 (d, 1H, J=8.2 Hz, 5-H), 4.30 (dd, 1H, J=5.3, 2.2 Hz, 3'-H), 4.02 (m, 1H, 4'-H), 3.76 (m, 2H), 3.67 (m, 2H), 3.48 (dd, 1H, J=8.5, 5.4 Hz, 2'-H), 2.63 (m, 2H), 1.74 (m, 2H), 1.57 (m, 2H); $^{13}$C NMR (75.5 MHz, CD$_3$OD) δ 170.0, 166.0 (C4), 152.6 (C2), 142.6 (C6), 135.5, 124.3, 115.1, 103.5 (C5), 90.0, 88.1, 73.6, 63.1, 54.7, 44.0, 38.3, 31.9, 28.6; MS (MALDI-TOF) calcd (M+Na$^+$) 484.5, found 484.5.

2'-Deoxy-2'-S-(4-ethoxycarbonylbutyl)uridine (Compound 2d)

Compound 2d was prepared by alkylating 2'-deoxy-2'-mercaptouridine with ethyl 5-bromovalerate according to the procedure used for the preparation of compound 2c above. $^1$H NMR (300 MHz, CD$_3$OD) δ 8.05 (d, 1H, J=8.2 Hz, 6-H), 6.10 (d, 1H, J=8.5 Hz, 1'-H), 5.78 (d, 1H, J=8.2 Hz, 5 -H), 4.32 (dd, 1H, J=5.4, 2.2 Hz, 3'-H), 4.10 (q, 2H, J=7.1 Hz), 4.02 (m, 4'-H), 3.78 (m, 2H, 5', 5"-H), 3.49 (dd, 1H, J=8.5, 5.4 Hz, 2'-H), 2.57 (t, 2H, J=7.1 Hz), 2.29 (t, 2H, J=7.4 Hz), 1.69-1.51 (m, 4H), 1.22 (t, 3H, J=7.1 Hz); $^{13}$C NMR (75.5 MHz, CD$_3$OD) δ 175.2, 165.8 (C4), 152.5 (C2), 142.6 (C6), 103.5 (C5), 89.8, 88.2, 73.6, 63.1, 61.5, 54.5, 44.0, 34.6, 32.1, 25.0, 14.7; MS (MALDI-TOF) calcd (M+Na$^+$) 411.4, found 411.4.

Compound 2a

Compound 2a was prepared by alkylating 2'-deoxy-2'-mercaptouridine with compound 1a according to the procedure used for the preparation of compound 2c above. $^1$H NMR (300 MHz, CD$_3$OD) δ 7.99 (d, 1H, J=8.2 Hz, 6-H), 7.75-7.56 (m, 8H), 6.07 (d, 1H, J=8.5 Hz, 1'-H), 5.65 (d, 1H, J=8.2 Hz, 5-H), 4.18 (dd, 1H, J=5.4, 2.2 Hz, 3'-H), 3.93 (m, 1H, 4'-H), 3.72-2.52 (m, 7H), 2.73 (m, 2H), 1.90-1.60 (m, 4H), 1.41 (m, 1H); $^{13}$C NMR (75.5 MHz, CD$_3$OD) δ 170.1, 170.0, 166.1 (C4), 152.6 (C2), 142.6 (C6), 135.4, 133.5, 133.4, 124.2, 103.5 (C5), 90.0, 87.9, 73.2, 63.1, 55.0, 36.44, 36.36, 34.7, 33.01, 32.89; MS (MALDI-TOF) calcd (M+Na$^+$) 657.7, found 657.4.

Compound 2b

Compound 2b was prepared by alkylating 2'-deoxy-2'-mercaptouridine with the crude compound 1b according to the procedure used for the preparation of compound 2c above. $^1$H NMR (200 MHz, CD$_3$OD) δ 8.00 (d, 1H, J=8.2 Hz, 6-H), 7.34 (m, 10H), 6.11 (d, 1H, J=8.5 Hz, 1'-H), 5.70 (d, 1H, J=8.2 Hz, 5-H), 5.10 (s, 4H), 4.32 (dd, 1H, J=5.3, 2.2 Hz, 3'-H), 4.01 (m, 1H, 4'-H), 3.77 (m, 2H, 5', 5''-H), 3.45 (dd, 1H, J=8.5, 5.4 Hz, 2'-H), 2.59 (m, 2H), 2.37 (m, 4H), 1.72-1.53 (m, 5H); MS (MALDI-TOF) calcd (M+Na$^+$) 635.7, found 635.9.

5'-O-DMT-2'-deoxy-2'-S-(4-phthalimidylbutyl)uridine (Compound 3c)

Compound 2c (693 mg, 1.5 mmol) was dissolved in anhydrous pyridine (12 mL). 4,4'-Dimethoxytrityl chloride (250 mg, 0.74 mmol) was added and the solution was kept stirring at room temperature. Another batch of 4,4'-dimethoxytrityl chloride (258 mg, 0.76 mmol) was added into the solution after 1 h and the mixture was kept stirring for one more hour before quenched by CH$_3$OH (1 mL) The solution was stirred for another 5 min before the solvent was removed under vacuum. The residue was dissolved in EtOAc (150 mL) and washed with saturated NaHCO$_3$ (2×50 mL) and brine (50 mL) sequentially. The organic layer was dried over Na$_2$SO$_4$. The solvent was then removed under vacuum and the crude product was subjected to silica chromatography using EtOAc/CH$_2$Cl$_2$ (from 0/100 to 4/100) containing 0.5% TEA as eluant to give the pure product (937 mg). The yield was 82%. $^1$H NMR (300 MHz, CDCl$_3$) δ 7.79 (m, 3H), 7.68 (m, 2H), 7.38-7.20 (m, 9H), 6.82 (d, 4H, J=8.9 Hz), 6.05 (d, 1H, J=3.4 Hz, 1'-H), 5.35 (d, 1H, J=8.2 Hz, 5-H), 4.40 (m, 1H, 3'-H), 4.12 (m, 1H, 4'-H), 3.79 (s, 6H), 3.68 (m, 2H), 3.50 (m, 3H), 2.72 (t, 2H, J=7.1 Hz), 1.80 (m, 2H), 1.66 (m, 2H); $^{13}$C NMR (75.5 MHz, CDCl$_3$) δ 168.6, 163.1 (C4), 158.9, 150.4 (C2), 144.4, 139.9 (C6), 135.3, 135.1, 134.2, 132.2, 130.3, 128.2, 127.4, 123.4, 113.5, 102.8 (C5), 87.9, 87.4, 84.8, 71.0, 63.2, 56.0, 55.4, 37.2, 31.9, 27.6, 27.0.

5'-O-DMT-2'-deoxy-2'-S-(4-ethoxycarbonylbutyl) uridine (Compound 3d)

Compound 2d was 5'-O-dimethoxytritylated according the procedure used for the preparation of compound 3c described above to give compound 3d. $^1$H NMR (300 MHz, CDCl$_3$) δ 7.80 (d, 1H, J=8.2 Hz, 6-H), 7.38-7.20 (m, 9H), 6.82 (d, 4H, J=8.9 Hz), 6.04 (d, 1H, J=3.4 Hz, 1'-H), 5.32 (d, 1H, J=8.2 Hz, 5-H), 4.39 (m, 1H, 3'-H), 4.13 (m, 1H, 4'-H), 4.09 (q, 2H, J=7.1 Hz), 3.78 (s, 6H), 3.74 (m, 2H, 51, 51'-H), 3.49 (m, 2H), 2.65 (t, 2H, J=7.1 Hz), 2.29 (t, 2H, J=7.4 Hz), 1.67 (m, 4H), 1.22 (t, 3H, J=7.1 Hz); $^{13}$C NMR (75.5 MHz, CDCl$_3$) δ 173.6, 163.7 (C4), 158.7, 150.6 (C2), 144.2, 140.0 (C6), 135.2, 135.0, 130.1, 128.1, 127.3, 113.3, 102.6 (C5), 87.9, 87.3, 84.7, 71.1, 63.2, 60.6, 55.3, 33.6, 31.8, 29.1, 23.8, 14.2.

5'-O-DMT-2'-deoxy-2'-S—[N-(trifluoroacetyl)-2-aminobutyl]uridine (Compound 3f)

Hydrazine (200 μL) was added in the methanolic (20 mL) solution of compound 3c (937 mg, 1.2 mmol). The solution was stirred at reflux for 3 h. After cooling, the solvent was removed under vacuum. The residue was re-dissolved in CH$_3$CN (2×10 mL) and evaporated to remove the residual hydrazine. The crude deprotected product 5'-O-DMT-2'-deoxy-2'-S-(4-aminobutyl)uridine was vacuum-dried before dissolving in dry CH$_3$OH (7.4 mL) followed by addition of triethylamine (TEA) (0.37 mL) and ethyl trifluoro-acetate (857 μL, 7.2 mmol). The solution was stirred at room temperature for 16 h before the solvent was evaporated under vacuum. The residue was dissolved in EtOAc (150 mL) and washed with 5% NaHCO$_3$ (2×50 mL) and brine (50 mL) sequentially. The organic layer was dried over Na$_2$SO$_4$. After the solvent was removed under vacuum, the crude product was subjected to silica chromatography using CH$_3$OH/CH$_2$Cl$_2$ (from 0/100 to 2/100) containing 0.2% TEA as eluant to obtain the pure product (670 mg). The yield was 77%. $^1$H NMR (300 MHz, CDCl$_3$) δ 7.98 (d, 1H, J=8.2 Hz, 6-H), 7.43 (s, 1H, N—H), 7.38-7.20 (m, 9H), 6.81 (d, 4H, J=8.9 Hz), 6.04 (d, 1H, J=3.4 Hz, 1'-H), 5.30 (d, 1H, J=8.2 Hz, 5-H), 5.28 (s, b, 1H, N—H), 4.49 (m, 1H, 3'-H), 4.07 (m, 1H, 4'-H), 3.79 (s, 6H), 3.50 (m, 3H), 3.34 (m, 2H), 2.73 (m, 2H), 1.70 (m, 4H); $^{13}$C NMR (75.5 MHz, CDCl$_3$) δ 163.6 (C4), 158.9, 157.6 (q, J=45.3 Hz, COCF$_3$), 151.2 (C2), 144.4, 140.1 (C6), 135.3, 135.1, 130.3, 128.2, 127.4, 116.1 (q, J=286.9 Hz, CF$_3$), 113.5, 102.8 (C5), 88.9, 87.5, 84.5, 70.2, 62.4, 55.9, 55.4, 39.3, 31.8, 27.7, 26.7.

Compound 3b

Compound 2b was 5'-O-dimethoxytritylated according the procedure used for the preparation of compound 3c described above to give compound 3b. $^1$H NMR (300 MHz, CDCl$_3$/CD$_3$OD) δ 7.80 (d, 1H, J=8.2 Hz, 6-H), 7.45-7.16 (m, 9H), 6.79 (d, 4H, J=8.9 Hz), 6.01 (d, 1H, J=3.5 Hz, 1'-H), 5.28 (d, 1H, J=8.2 Hz, 5-H), 5.03 (s, 4H), 4.40 (m, 1H, 3'-H), 4.07 (m, 1H, 4'-H), 3.73 (s, 6H), 3.43 (m, 2H), 3.38 (m, 1H), 2.63 (m, 2H), 2.42 (m, 4H), 1.80-1.58 (m, 5H); $^{13}$C NMR (75.5 MHz, CDCl$_3$) δ 173.6, 173.5, 163.7 (C4), 158.8, 150.6 (C2), 144.4, 140.1 (C6), 135.9, 135.8, 135.3, 135.2, 130.2, 128.7, 128.4, 128.2, 128.1, 127.3, 113.4, 102.6 (C5), 88.4, 87.3, 84.6, 70.7, 66.6, 62.8, 55.6, 55.4, 37.1, 35.9, 31.4, 27.9.

Compound 3e

Compound 2a was 5'-O-dimethoxytritylated according the procedure used for the preparation of compound 3c described above to give compound 3a. $^1$H NMR (300 MHz, CDCl$_3$) δ 7.82 (d, 1H, J=8.2 Hz, 6-H), 7.70 (m, 8H), 7.40-7.18 (m, 9H), 6.83 (d, 4H, J=8.8 Hz), 6.08 (d, 1H, J=3.5 Hz, 1'-H), 5.35 (d, 1H, J=8.2 Hz, 5-H), 4.48 (m, 1H, 3'-H), 4.13 (m, 1H, 4'-H), 3.78 (s, 6H), 3.73 (m, 4H), 3.59 (m, 1H), 3.50 (m, 2H), 3.39 (s, b, 1H), 2.92 (m, 2H), 1.81 (m, 4H). Compound 3e was prepared from compound 3a according to the procedure for preparing compound 3f described above. $^1$H NMR (300 MHz, CDCl$_3$) δ 8.04 (d, 1H, J=8.2 Hz, 6-H), 7.65 (s, b, 1H, 7.65, N—H), 7.40-7.20 (m, 9H), 6.81 (d, 4H, J=8.8 Hz), 6.00 (d, 1H, J=3.4 Hz, 1'-H), 5.27 (d, 1H, J=8.2 Hz, 5-H), 4.58 (dd, 1H, J=6.3, 4.6 Hz, 3'-H), 4.02 (m, 1H, 4'-H), 3.77 (s, 6H), 3.53-3.30 (m, 7H), 2.83 (m, 2H), 1.85-1.60 (m, 5H); $^{13}$C NMR (75.5 MHz, CDCl$_3$) δ 163.0 (C4), 159.2, 157.8 (m, COCF$_3$), 151.3 (C2), 144.6, 140.0 (C6), 135.6, 130.4, 128.5, 128.2, 127.5, 113.7, 102.9 (C5), 89.7, 87.7, 84.5, 70.2, 62.3, 55.5, 37.6, 36.3, 32.6.

3'-O-[(2-cyanoethyl)(diisopropylamino)]phosphino-5'-O-DMT-2'-deoxy-2'-S-(4-ethoxycarbonylbutyl) uridine (Compound 4d)

Compound 3d (539 mg, 0.78 mmol) was dissolved in dry CH$_2$Cl$_2$ (4.7 mL) followed by addition of a catalytic amount of DMAP (~2 mg), TEA (435 μL, 3.1 mmol), and 2-cyanoethyl chlorodiisopropylamino phosphoramidite (312 μL, 1.4 mmol). After 30 min, the solvent was removed under vacuum and the residue was dissolved in EtOAc (100 mL) and washed with 5% NaHCO$_3$ (2×30 mL) and brine (30 mL) sequentially. The organic layer was dried over Na$_2$SO$_4$. After the solvent was removed under vacuum, the crude product was subjected to silica chromatography (CH$_2$Cl$_2$/EtOAc, from 100/0 to 100/

25, with 0.2% TEA) to yield 492 mg pure product. The yield was 71%. $^1$H NMR (300 MHz, CDCl$_3$) δ 8.66 (s, b, 1H, N—H), 7.84 (m, 1H, 6-H), 7.40-7.10 (m, 9H), 6.85-6.70 (m, 4H), 6.18 (m, 1H, 1'-H), 5.29 (m, 1H, 5-H), 4.63 (m, 1H, 3'-H), 4.22 (m, 1H, 4'-H), 4.13-3.90 (m, 4H), 3.80-3.40 (m, 11H), 2.63 (m, 4H), 2.27 (m, 2H), 1.78-1.50 (m, 4H), 1.29-1.03 (m, 15H); $^{31}$P NMR (121 MHz, CDCl$_3$) δ 151.0, 150.5.

3'-O-[(2-cyanoethyl)(diisopropylamino)]phosphino-5'-O-DMT-2'-deoxy-2'-S—[N-(trifluoroacetyl)-2-aminobutyl]uridine (Compound 4f)

The phosphitylation of compound 3f was performed according to the method to prepare compound 4d described above to give compound 4f. $^1$H NMR (300 MHz, CDCl$_3$) δ 8.02 (m, 1H, 6-H), 7.48-7.20 (m, 10H), 6.83 (m, 4H), 6.12 (m, 1H, 1'-H), 5.20 (m, 1H, 5-H), 4.77 (m, 1H, 3'-H), 4.26-3.77 (m, 9H), 3.67-3.30 (m, 7H), 2.78-2.62 (m, 4H), 1.70 (m, 4H), 1.29-1.03 (m, 12H); $^{31}$P NMR (121 MHz, CDCl$_3$) δ 150.8 (s, b).

Compound 4b

The phosphitylation of compound 3b was performed according to the method to prepare compound 4d described above to give compound 4b. $^1$H NMR (300 MHz, CDCl$_3$) δ 8.39 (s, b, N—H), 7.88 (m, 1H, 6-H), 7.39-7.20 (m, 9H), 6.80 (m, 4H), 6.11 (m, 1H, 1'-H), 5.23 (m, 1H, 5-H), 5.06 (s, 4H), 4.65 (m, 1H, 3'-H), 4.25-4.10 (m, 3H), 3.76 (s, 6H), 3.59-3.42 (m, 5H), 2.78-2.63 (m, 4H), 2.35 (m, 4H), 1.70 (m, 4H), 1.29-1.03 (m, 12H); $^{31}$P NMR (121 MHz, CDCl$_3$) δ 150.5, 150.4.

Compound 4e

The phosphitylation of compound 3e was performed according to the method to prepare compound 4d described above to give compound 4e. $^1$H NMR (300 MHz, CDCl$_3$) δ 9.20 (s, b, 1H, N—H), 8.00 (m, 1H, 6-H), 7.38-7.20 (m, 9H), 6.80 (m, 4H), 5.85 (m, 1H, 1'-H), 5.25 (m, 1H, 5-H), 4.66 (m, 1H, 3'-H)), 4.21-4.00 (m, 3H), 3.77 (s, 6H), 3.60-3.21 (m, 9H), 2.77 -2.65 (m, 4H), 2.15-1.65 (m, 5H), 1.29-1.03 (m, 12H); $^{31}$P NMR (121 MHz, CDCl$_3$) δ 150.8, 150.5.

General Procedure for Oligonucleotide Synthesis

The phosphoramidites used in this study were diluted to 0.1M using dry CH$_3$CN. The commercially available T phosphoramidites was purchased from Applied Biosystems, and the syntheses of the 4b, 4d-f phosphoramidites are described above.

The oligonucleotides described in this study were synthesized on an Applied Biosystems 380B automatic DNA synthesizer using routine phosphoramidite procedures (Caruthers, 1985), however at the point where the sequence contained either 4b, 4d, 4e, or 4f the coupling time was increased to 30 min.

Cleavage of ODN from the synthesis support was carried out by taking the CPG column and placing it in an Eppendorf tube containing 1000 μL of 10% (v/v) piperidine in 0.2 N NaOH/MeOH. This tube was shaken overnight, spun down and the supernatant added and thoroughly mixed with 200 μL 890 mM Tris.HCl, pH 8.3, 890 mM boric acid, 20 mM EDTA (10×TBE). The solution was evaporated to ca. 600 μL and a 50 μL aliquot was filtered through two Microspin Sephadex G25 columns (Amersham Biosciences). The DNA in the resulting solution was quantitated using UV spectroscopy (OD$_{260}$).

Before each coupling reaction, an aliquot of this material was brought to 200 μL in 0.5-1 M NH$_4$Cl. 1000 μL of 100% ethanol was added, and the solution chilled to −78° C. for 45 min. The solution was spun at 13,000 rcf for 30 min, the supernatant discarded and the solution re-dissolved in 200 μL 0.5-1 M NH$_4$Cl. The precipitation/spinning/re-dissolution procedure was repeated twice, the pellet washed with 500 μL 70% ethanol (−20° C.) and dried before re-suspended in water.

General Procedure for Amide Bond Formation

Condensing agent 4-(4,6-Dimethoxy-1,3,5-triazin-2-yl)-4-methylmorpholinium chloride (DMT-MM) (13.8 mg, 0.05 mmol) was dissolved in MOPS buffer (0.1 M, 1.0 M NaCl, pH 7.0, 1.0 mL). The resulted DMT-MM solution (50 nM, 10 μL) was added in an Eppendorf vial containing ODN (200 pmol) modified with amino and carboxyl groups. The reaction mixture was well-vortexed and centrifuged before being kept at room temperature for 48 h. 300 μL of water was added to the sample and the solution was extracted with 600 μL butanol. The solution was brought to 1 M NH$_4$Cl and 1000 μL of ethanol was added. The solution was chilled to −78° C. for 45 min and then spun at 13,000 rcf for 30 min, the supernatant poured off and the solution re-dissolved in water.

General Procedure for MALDI-TOF MS Analysis

THAP matrix stock solution (0.2 M) in CH$_3$CN/H$_2$O (1:1 v:v) was prepared by dissolving THAP (33 mg, 0.2 mmol) in CH$_3$CN (0.5 mL) and H$_2$O (0.5 mL). This stock solution can be used up to 3 weeks or so if stored at −20° C. A working matrix solution was prepared immediately before the measurement by mixing the stock solution (30 μL) and co-matrix ammonium tartrate solution (0.1 M in deionized H$_2$O, 70 μL). An ODN sample (1-10 pmole/μL, 0.5 μL) was mixed with the working matrix solution (5 μL) using a vortex, and the heterogeneous mixture was spun at 13,000 rcf for 25 sec. 1 μL of the supernatant was deposited in each well on a 7×7 target. Bovine insulin or ODNs with known masses were used as either external or internal calibrants in the measurements. Proper laser power was applied on a case by case basis.

Results

Figure 3:
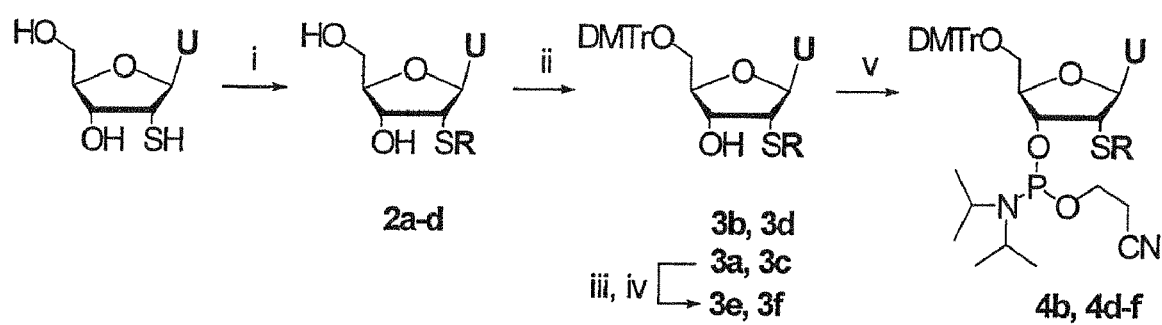
FIG. 3 shows a scheme of the synthesis of 2'-deoxy-2'-alkylthiouridine phosphoramidites, where the reagents and conditions are as follows: (i) RI (1a, 1b) or RBr (1c, 1d), DIEA/CH$_3$CN, rt, 10 h; (ii) DMTrCl/pyridine, rt, 2 h; (iii) NH$_2$NH$_2$/CH$_3$OH, reflux, 3 h; (iv) CF$_3$CO$_2$Et/CH$_3$OH, rt, 16 h; (v) ClP(NiPr)$_2$(OCH$_2$CH$_2$CN)/CH$_2$Cl$_2$, TEA, DMAP, rt, 30 min. (a: R=CH$_2$CH(CH$_2$CH$_2$NPhth)$_2$; b: R=CH$_2$CH(CH$_2$CH$_2$CO$_2$Bn)$_2$; c: R=(CH$_2$)$_4$NPhth; d: R=(CH$_2$)$_4$CO$_2$Et; e: R=CH$_2$CH(CH$_2$CH$_2$NHCOCF$_3$)$_2$; f: R=(CH$_2$)$_4$NHCOCF$_3$).
Figure 4:
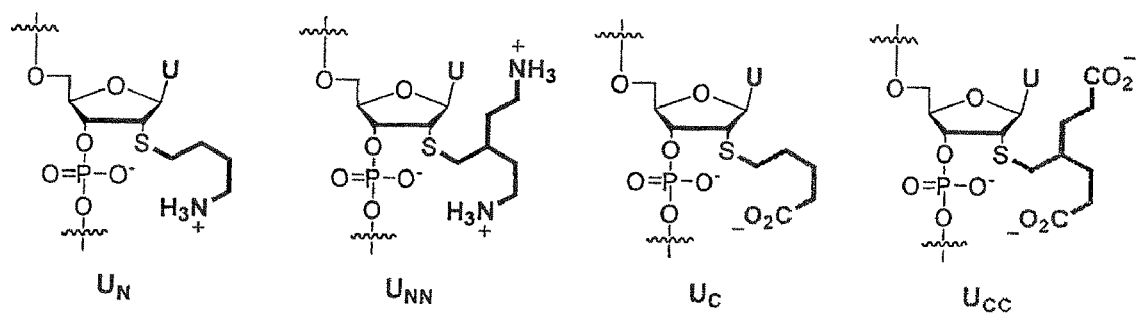
FIG. 4 shows the structures of 2'-modified nucleotidyl units.

Initial synthetic protocols attempted 2'-OH alkylation of a protected ribonucleoside, but this approach was inefficient for hindered electrophiles (Zhu et al., 2002). However, 2'-deoxy-2'-mercaptouridine[13] was alkylated with 1a and 1b to afford 2'-S-alkylated nucleosides exclusively (FIG. 3). Tritylation and phosphitylation of 2b afforded the modified phosphoramidite 4b. Two extra steps were taken to replace the stable phthalimidyl groups in 3a with DNA synthesizer-friendly trifluoroacetyl groups (Telser et al., 1989). Phosphitylation of the resulting nucleoside 3e afforded amino-modified phosphoramidite 4e. Mono-amino and carboxyl modified phosphoramidites 4d and 4f were prepared by similar methods. The respective nucleotidyl groups are shown in deprotected form in FIG. 4.

Modified phosphoramidites were incorporated into 16-mer ODNs through conventional ODN synthesis. The sequences are shown in Table 1.

TABLE 1

Sequences and MALDI-TOF MS characterization of synthetic ODNs.

| | | | | m/z [M − 1]⁻ | |
|---|---|---|---|---|---|
| ODN No. | ODN Sequence | Calcd. | Found | Coupled Calcd. | Coupled Found |
| 1 | 5'-(dT)$_6$U$_N$U$_C$(dT)$_8$ | 5011.4 | 5011.4 | 1C - 4993.4 | 1C - 4993.7 |
| 2 | 5'-(dT)$_3$U$_N$U$_C$(dT)$_2$U$_N$U$_C$(dT)$_2$U$_N$U$_C$(dT)$_3$ | 5426.0 | 5427.0 | 2C - 5372.0 | 2C - 5371.4 |
| 3 | 5'-(dT)$_7$U$_N$U$_{CC}$U$_N$(dT)$_6$ | 5172.7 | 5172.4 | 3C - 5136.6 | 3C - 5136.2 |
| 4 | 5'-(dT)$_7$U$_C$U$_{NN}$U$_C$(dT)$_6$ | 5172.7 | 5172.8 | 4C - 5136.6 | 4C - 5136.9 |
| 5 | 5'-(dT)$_6$U$_C$U$_{NN}$U$_{CC}$U$_N$(dT)$_6$ | 5333.9 | 5333.6 | 5C - 5279.8 | 5C - 5280.3 |

Methanolic NaOH was used to deprotect and remove the strands from the CPG support. The conventional concentrated ammonium hydroxide treatment could not be used due to aminolysis between NH$_3$ and the ester moieties (Berthod et al., 1996). Deprotection with prevention of the Michael addition between acrylonitrile and deprotected amines (Avino et al., 1994) was accomplished by including 10% piperidine in methanolic NaOH. To prevent acetate ions (from hydrolysis of the 5'-acetyl groups of the capped failure strands) from competing as alternative coupling partners, they were eliminated by triple ethanol precipitation prior to being subjected to amide coupling conditions. The concurrent deprotection of amino and carboxyl groups and the removal of ODNs from CPG support was therefore achieved with this customized protocol. The ODNs were characterized by MALDI-TOF mass spectrometry (Pieles et al., 1993 and Li et al., 1998) (Table 1).

Figure 5:
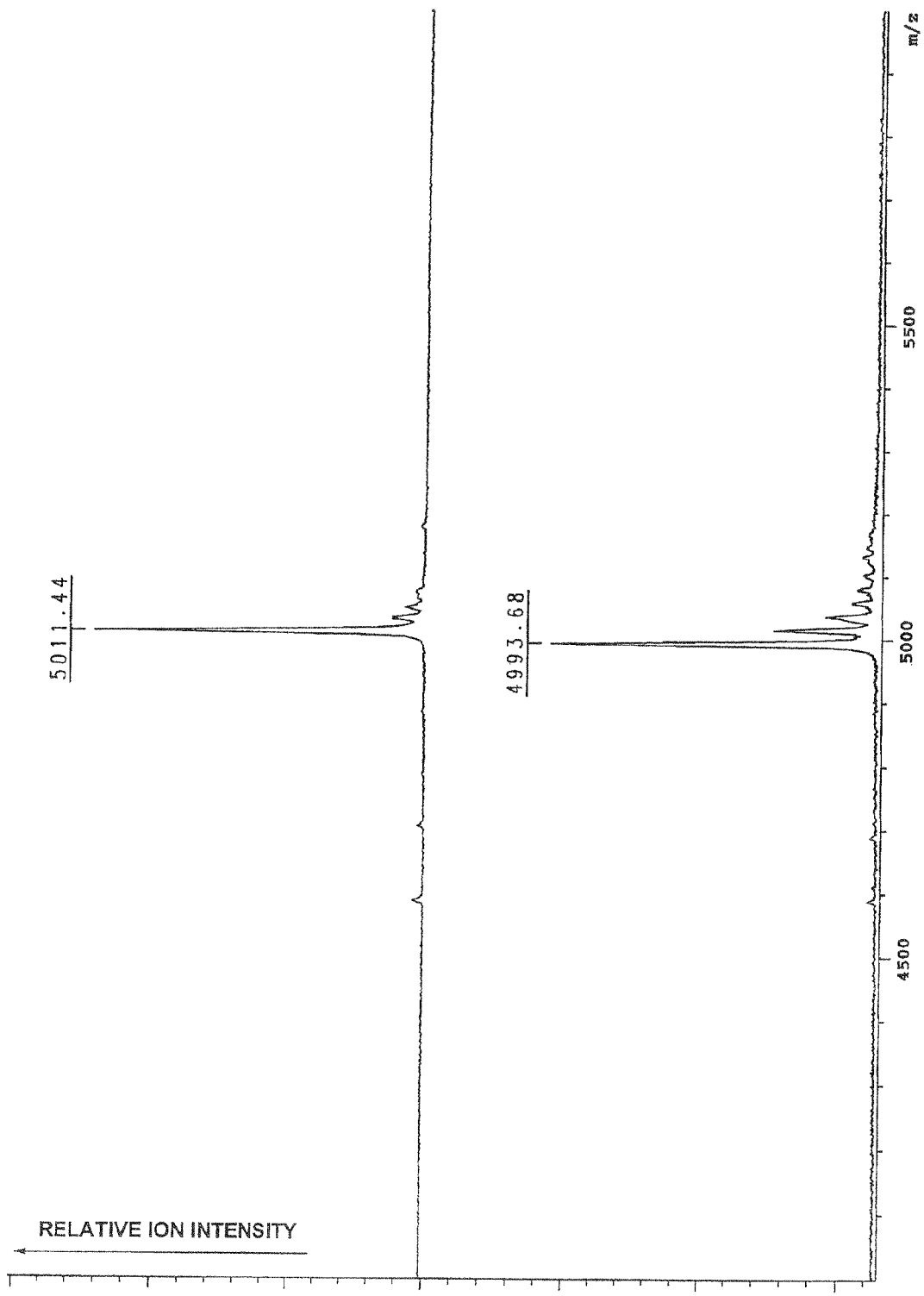
FIG. 5 shows the matrix-assisted laser desorption ionization-time-of-flight (MALDI-TOF) mass spectroscopy spectra of uncoupled ODN 1, 5' (dT)$_6$U$_N$U$_C$(dT)$_8$ (top), and the coupled strand product 1C (bottom).
Figure 6:
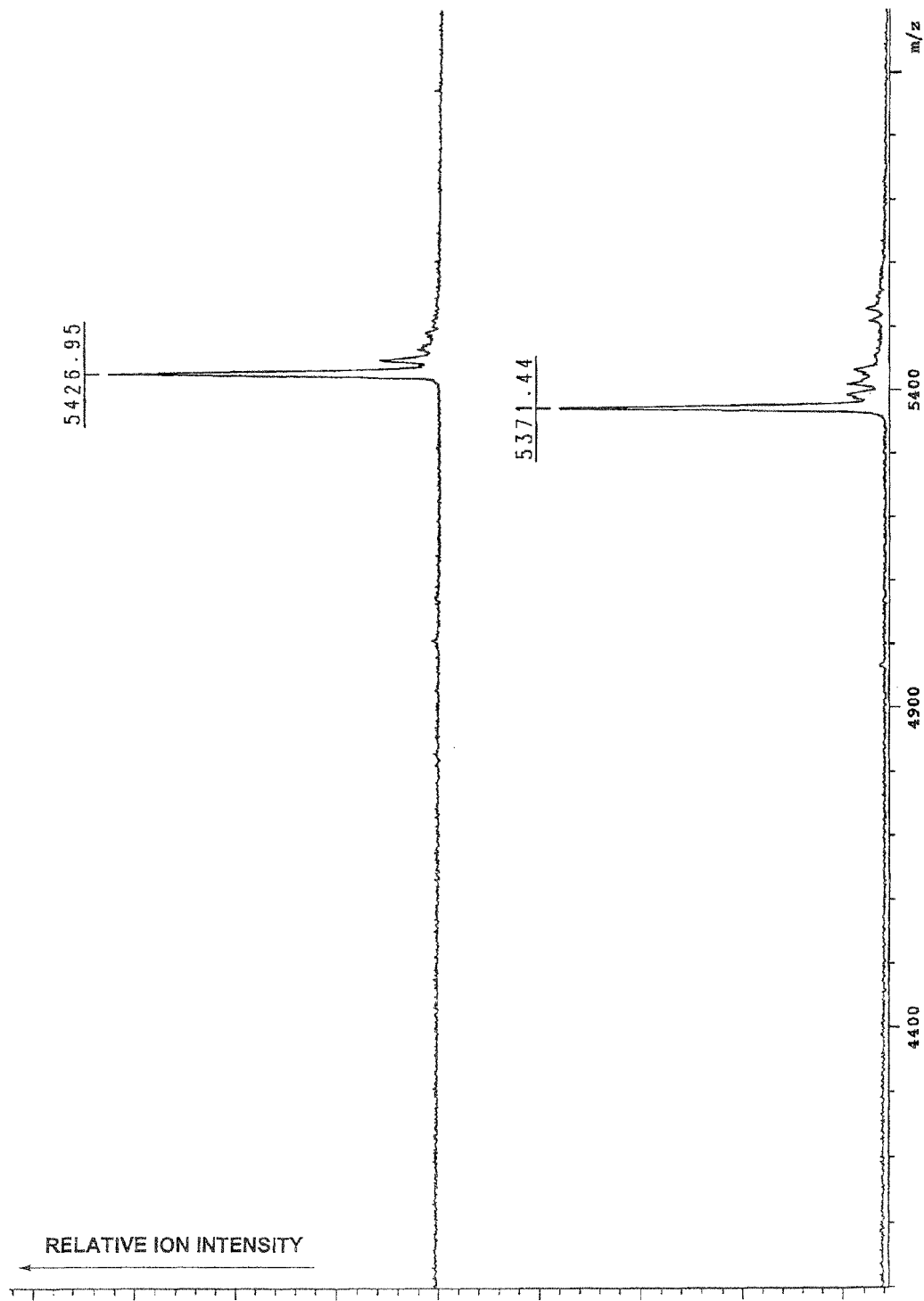
FIG. 6 shows the MALDI-TOF mass spectroscopy spectra of uncoupled ODN 2, 5' (dT)$_3$U$_N$U$_C$(dT)$_2$U$_N$U$_C$(dT)$_2$U$_N$U$_C$(dT)$_3$ (top), and the coupled strand product 2C (bottom).

ODN 1 was first subjected to amide coupling conditions. Both condensing agents DMT-MM (4-(4,6-Dimethoxy-1,3,5-triazin-2-yl)-methylmorpholinium chloride; Kunishima et al. 2001 and Liu et al., 2002) and EDC (N-Ethyl-N'-(dimethylaminopropyl)carbodiimide; Schmidt et al., 1997 and Seitz et al., 2001) proved effective in promoting the intra-strand amide forming reaction between U$_N$ and U$_C$ under various buffer conditions. DMT-MM was preferred, as it did not leave residual covalent adducts. The yield of the coupling reaction was estimated by MALDI-TOF analysis (Sarracino et al., 1996 and Berggren et al., 2002). The yield of ODN 1C from 1 was estimated to be more than 95% (FIG. 5), whereas the yield of 2C with 3 amide bonds was 78% (FIG. 6), which also put the single amide bond-forming yield over 95% (These estimates are lower limits, as small amounts of sodium in the spectra obscure and artificially inflate the starting material peak). A control coupling reaction using an ODN with regular T residues replacing U$_C$ in 2 showed no mass loss.

Figure 7:
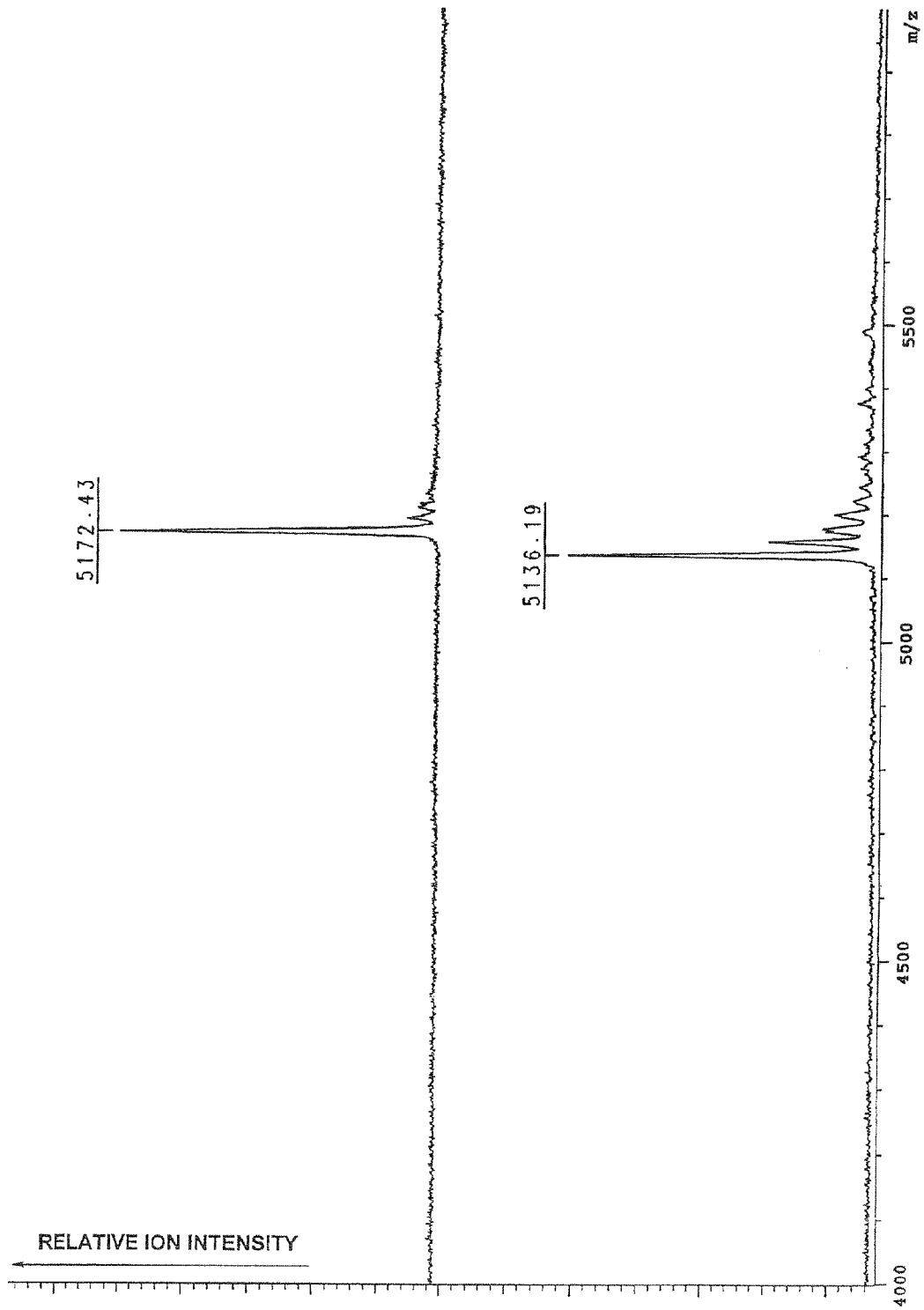
FIG. 7 shows to MALDI-TOF mass spectroscopy spectra of uncoupled ODN 3, 5'-(dT)$_7$U$_N$U$_{CC}$U$_N$(dT) 6 (top), and the coupled strand product 3C (bottom).
Figure 8:
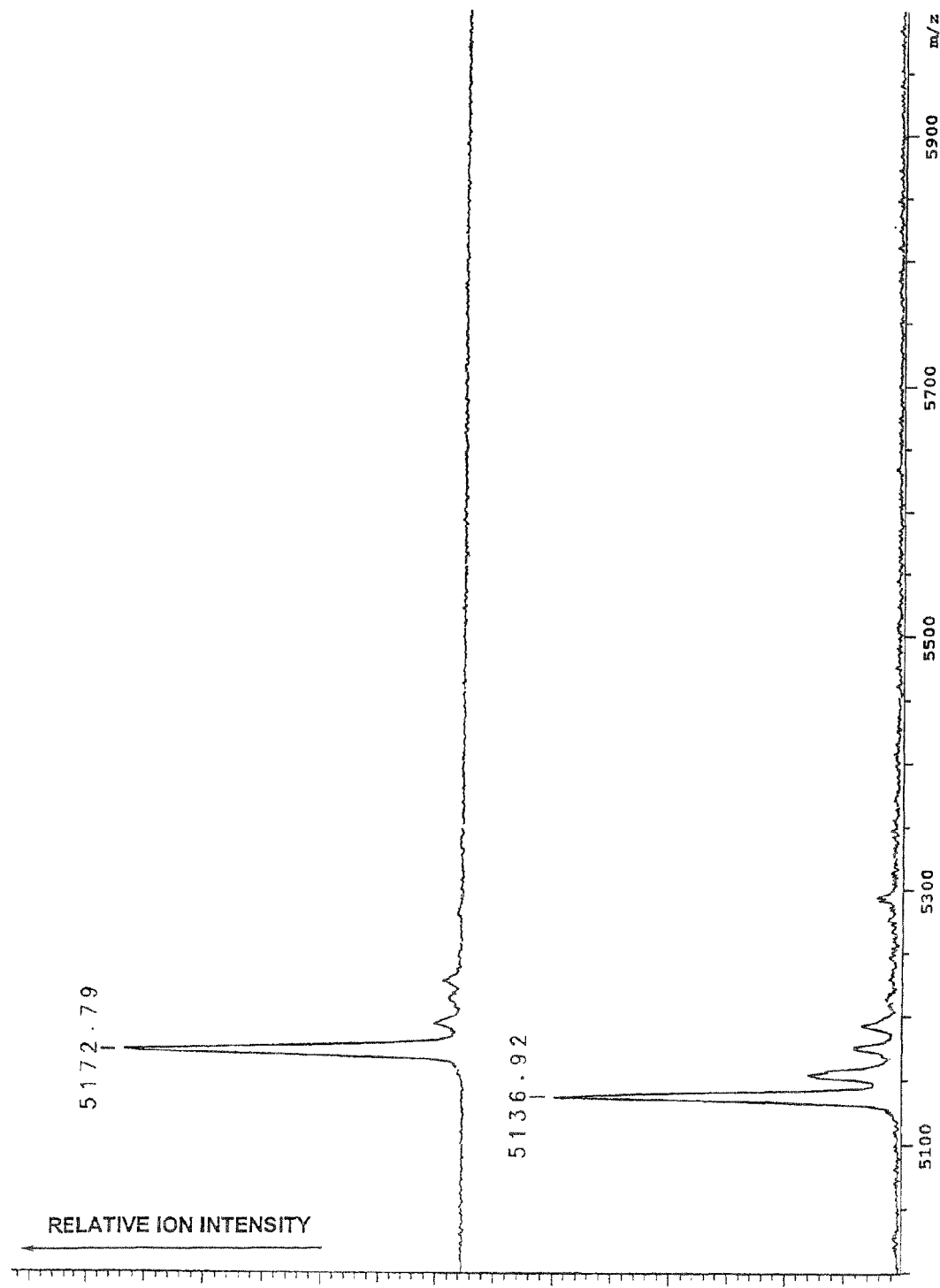
FIG. 8 shows the MALDI-TOF mass spectroscopy spectra of uncoupled ODN 4, 5'-(dT)$_7$U$_C$U$_{NN}$U$_C$(dT)$_6$ (top), and the coupled strand product 4C (bottom).
Figure 9:
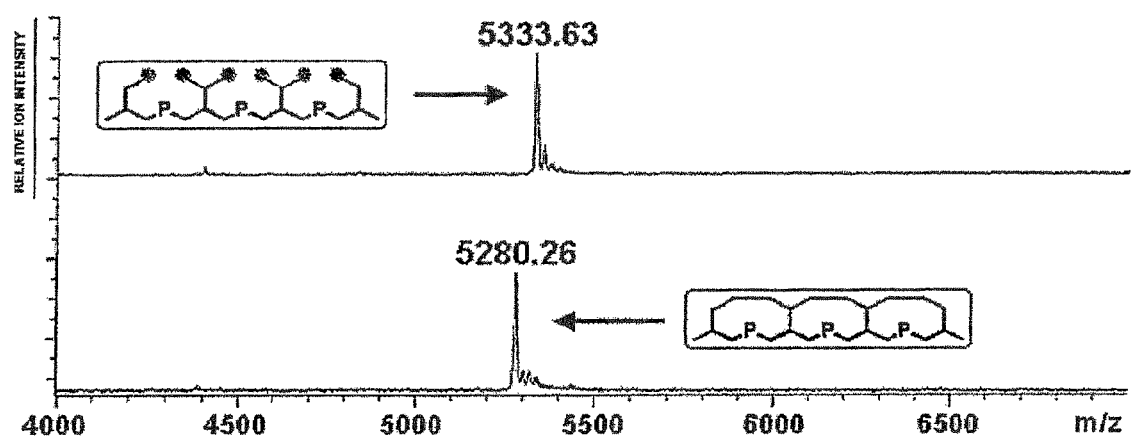
FIG. 9 shows the MALDI-TOF mass spectroscopy spectra of uncoupled ODN 5, 5'-(dT)$_6$U$_C$U$_{NN}$U$_{CC}$U$_N$(dT)$_6$ (top), and coupled strand product 5C (bottom).
Figure 10A:
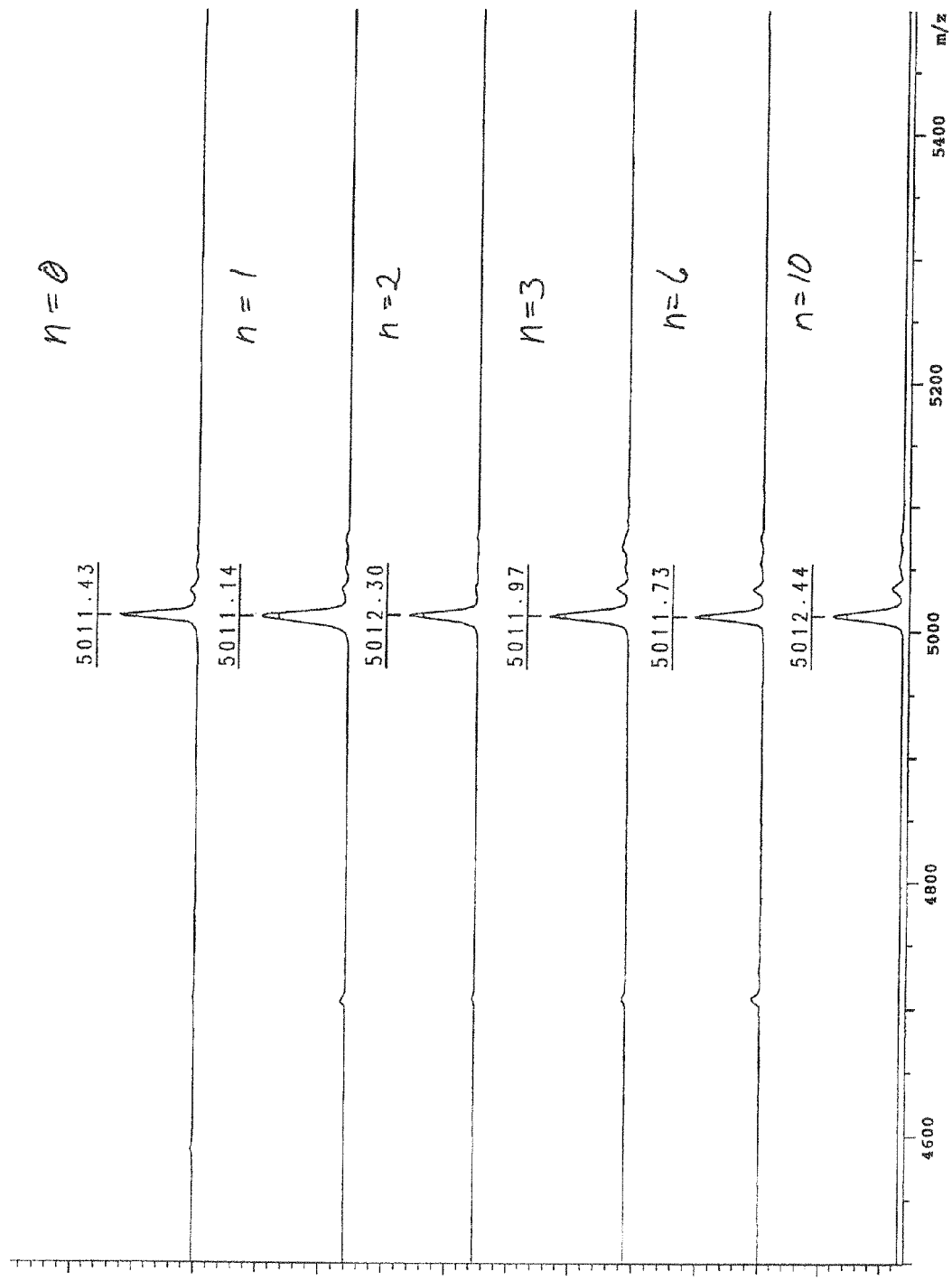
FIGS. 10A and 10B show the MALDI-TOF mass spectroscopy spectra of the ODN, 5'-(dT)$_x$U$_N$(dT)$_n$U$_C$(dT)$_y$ (x+n+y=14) before (FIG. 10A) and after (FIG. 10B) being treated under coupling conditions.
Figure 10B:
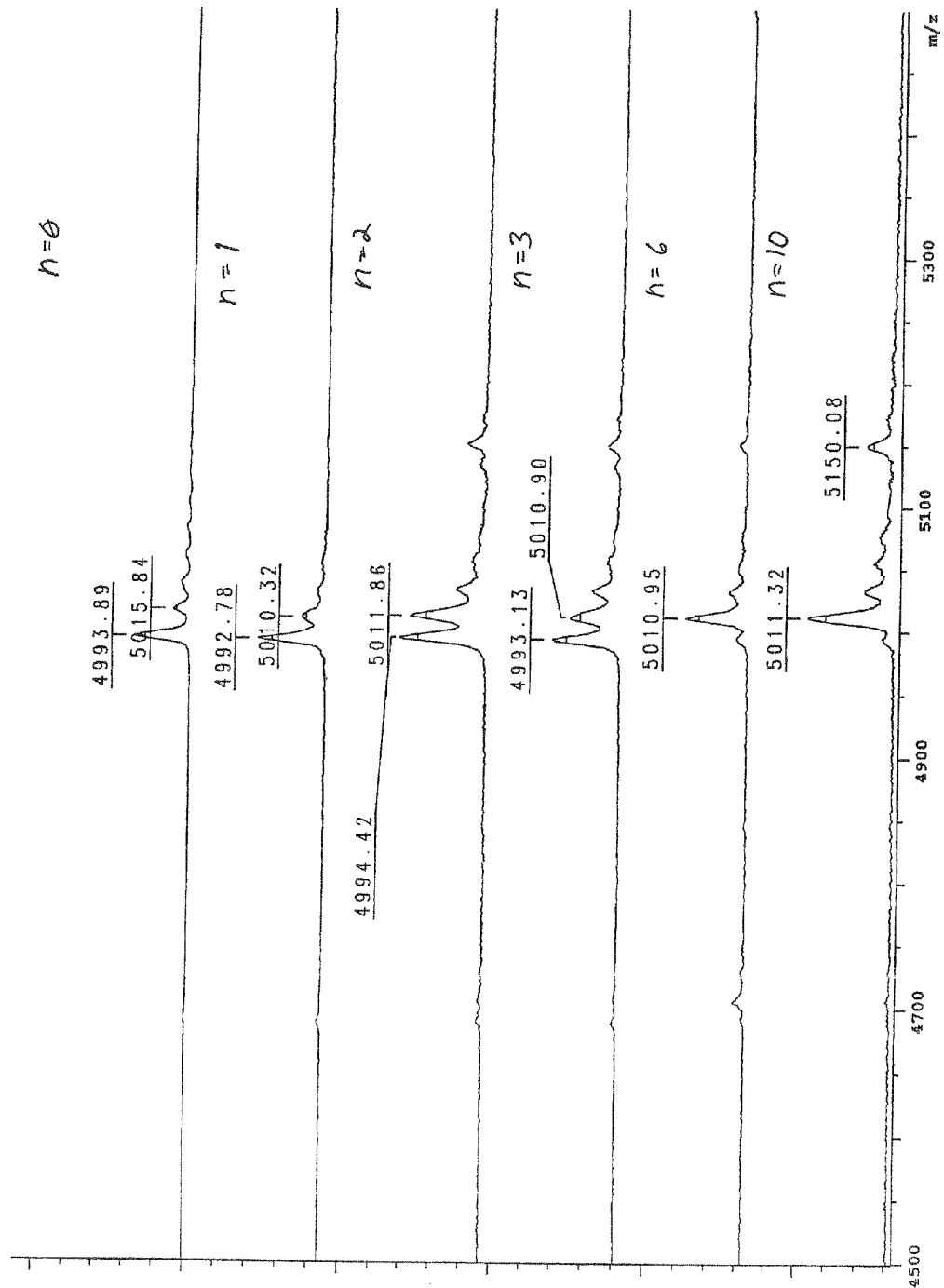
Figure 11:
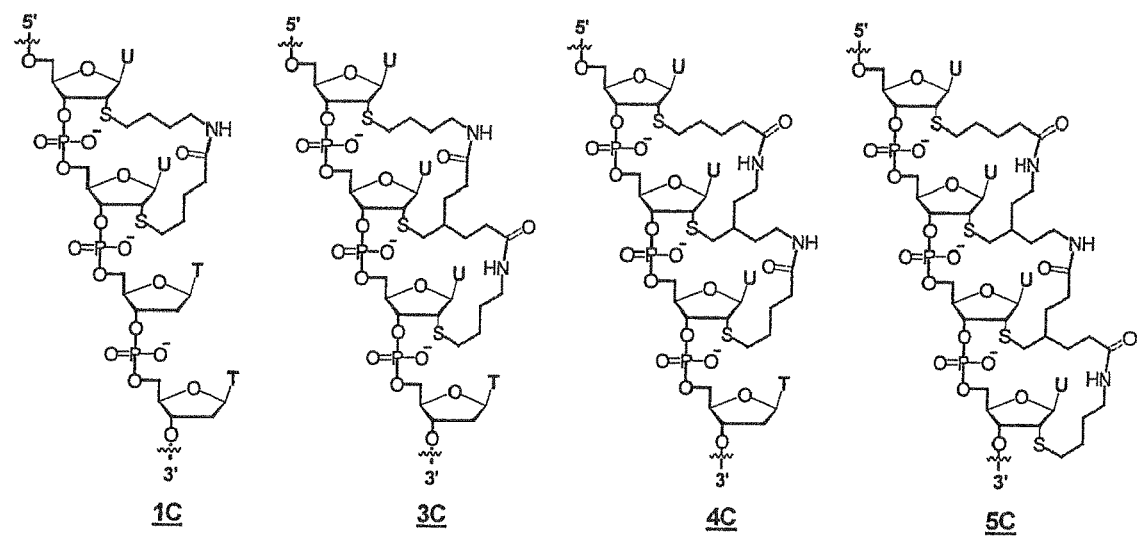
FIG. 11 shows the chemical structures of DNA-nylon conjugates 1C, 3C, 4C, and 5C.

Isomers 3 and 4 were treated under coupling conditions to afford ODNs with two amide bonds closing two fused 21-member rings containing both a phosphodiester backbone and the newly formed aliphatic carboxamide structure, as characterized by MALDI-TOF MS (Table 1; FIGS. 7 and 8). The condensation of ODN 5 yielded three amide bonds to form 5C (FIG. 9) with three fused 21-member rings. In 5C, a less likely topological isomer is possible under these reaction conditions. Control experiments were performed to study the distance dependence of the coupling reaction between amino and carboxyl groups separated by a spacer (FIGS. 10A and 10B), where strands 5'-(dT)$_x$U$_C$(dT)$_n$U$_N$(dT)$_y$ (x+n+y=14, n=0, 1, 2, 3, 6, 10) were subjected to amide-bond promoting conditions. It was found that the coupling yield did highly depend on the length of the spacer (dT)$_n$. When n≥2, the yield was less than 50%; when n=6 or 10, there were barely detectable coupled products. Therefore, the amide bonds were biased to form between amino and carboxyl groups on adjacent nucleotidyl residues. Structures of several of the product strands are indicated in FIG. 11. The linear polyamide backbone is essentially Nylon-5,7.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Avino, A. M.; Eritja, R., *Nucleosides Nucleotides,* 13:2059 (1994)

Barawkar, D. A.; Bruice, T. C., *J. Am. Chem. Soc.,* 121:10418 (1999)

Berggren, W. T.; Takova, T.; Olson, M. C.; E is, P. S.; Kwiatkowski, R. W.; Smith, L. M., Multiplexed gene expression analysis using the invader RNA assay with MALDI-TOF mass spectrometry detection, *Anal. Chem.,* 74:1745 (2002)

Berthod, T.; Pétillot, Y.; Guy, A.; Cadet, J.; Molko, D., *Org. Chem.,* 61:6075 (1996)

Caruthers, Gene synthesis machines: DNA chemistry and its uses, *Science,* 230:281 (1985)

Chaput, J. C.; Ichida, J. K.; Szostak, J. W., DNA polymerase-mediated DNA synthesis on a TNA template, *J. Am. Chem. Soc.,* 125:856 (2003)

Couzin, J., Breakthrough of the year. Small RNAs make big splash, *Science,* 298:2296 (2002)

Demidov, V. V., *Trends Biotech.,* 21:4 (2003)

Dennis, C., The brave new world of RNA, *Nature,* 418:122 (2002)

Divakar, K. J.; Mottoh, A.; Reese, C. B.; Sanghvi, Y. S., *Chem. Soc. Perkin Trans.* 1, 969 (1990)

Divakar et al., *J. Chem. Soc. Perkin Trans.* 1, 1625 (1982)

Du, S. M.; Stollar, B. D. and Seeman, N. C., A Synthetic DNA Molecule in Three Knotted Topologies, *Journal of the American Chemical Society* 117:1194-1200 (1995)

Du, S. M. and Seeman, N. C., The Synthesis of a DNA Knot Containing both Positive and Negative Nodes, *Journal of the American Chemical Society* 114:9652-9655 (1992)

Freier, S. M. and Altmann, K., The ups and downs of nucleic acid duplex stability: structure-stability studies on chemically-modified DNA:RNA duplexes, *Nucleic Acids Research,* 25 (22) 4429-4443 (1997)

Gartner, Z. J.; Kanan, M. W.; Liu, D. R., *J. Am. Chem. Soc.,* 124:10304 (2002)

Kunishima, M.; Kawachi, C.; Hioki, K.; Terao, K.; Tani, S., *Tetrahedron,* 57:1551 (2001)

Lermer, L.; Roupioz, Y.; Ting, R.; Perrin, D. M., Toward an RNaseA mimic: A DNAzyme with imidazoles and cationic amines, *J. Am. Chem. Soc.,* 124:9960 (2002)

Li, X.; Zhan, Z.-Y. J.; Knipe, R.; Lynn, D. G., *J. Am. Chem. Soc.,* 124:746 (2002)

Li, Y. C. L.; Cheng, S.-W.; Chan, T.-W. D., *Rapid Commun. Mass Spectrom.,* 12:993 (1998)

Liu, D. R.; Gartner, Z. J.; Kanan, M. W., *Angew. Chem. Int. Ed.,* 41:1796 (2002)

Mueller, J. E.; Du, S. M. and Seeman, N. C., The Design and Synthesis of a Knot from Single-Stranded DNA, *Journal of the American Chemical Society* 113:6306-6308 (1991)

Nielsen, *Acc. Chem. Res.,* 32:624 (1999) Ozaki, H.; Momiyama, S.; Yokotsuka, K.; Sawai, H., *Tetrahedron Lett.,* 42:677 (2001)

Pearson, H., DNA: Beyond the double helix, *Nature,* 421:312 (2003)

Pieles, U. Zürcher, W.; Schär, M.; Moser, H. E., Matrix-assisted laser desorption ionization time-of-flight mass spectrometry: a powerful tool for the mass and sequence analysis of natural and modified oligonucleotides, *Nucleic Acid Res.,* 21:3191 (1993)

Santoro, S. W.; Joyce, G. F.; Sakthivel, K.; Gramatikova, S.; Barbas, C. F. III, RNA cleavage by a DNA enzyme with extended chemical functionality, *J. Am. Chem. Soc.,* 122:2433 (2000)

Sarracino, D.; Richert, C., *Bioorg. Med. Chem. Lett.,* 6:2543 (1996)

Schmidt, J. G.; Christensen, L.; Nielsen, P. E.; Orgel, L. E., *Nucleic Acids Res.,* 25:4792 (1997)

Schöning, K.-U.; Scholz, P.; Guntha, S.; Wu, X.; Krishnamurthy, R.; Eschenmoser, A., Chemical etiology of nucleic acid structure: the alpha-threofuranosyl-(3'- ->2') oligonucleotide system, *Science,* 290:1347 (2000)

Seeman N C., DNA in a material world, *Nature,* 421:427 (2003)

Seeman N C., DNA engineering and its application to nanotechnology, *Trends Biotech.,* 17:437 (1999)

Du, S. M. and Seeman, N. C., The Construction of a Trefoil Knot from a DNA Branched Junction Motif, *Biopolymers* 34:31-37 (1994)

Seeman, N. C.; Chen, J.; Du, S. M.; Mueller, J. E.; Zhang, Y.; Fu, T.-J.; Wang, H.; Wang, Y.; and Zhang, S., Synthetic DNA Knots and Catenanes, *New Journal of Chemistry* 17:739-755 (1993)

Seeman, N. C., The Design of Single-Stranded Nucleic Acid Knots, *Molecular Engineering* 2:297-307 (1992)

Seitz, O.; Mattes, A., *Angew. Chem. Int. Ed.,* 40:3178 (2001)

Telser, J.; Cruickshank, K. A.; Morrison, L. E.; Netzel, T. L., *J. Am. Chem. Soc.,* 111:6966 (1989)

Thum, O.; Jäger, S.; Famulok, M., Functionalized DNA: A New Replicable Biopolymer We thank Dr. Andreas Marx, University of Bonn, for helpful advice and discussions. This work was supported by the Fonds der Chemischen Industrie, the Karl-Ziegler Stiftung, and the Deutsche Forschungsgemeinschaft, *Angew. Chem. Int. Ed.,* 40:3990 (2001)

Uhlmann, E.; Peyman, A., *Chem. Rev.,* 90:543 (1990)

Vester, B.; Lundberg, L. B.; Sørensen, M. D.; Babu, B. R.; Douthwaite, S.; Wengel, J., LNAzymes: incorporation of LNA-type monomers into DNAzymes markedly increases RNA cleavage, *J. Am. Chem. Soc.,* 124:13682 (2002)

Wang, H.; Du, S. M. and Seeman, N. C., Tight Single-Stranded DNA Knots, *Journal of Biomolecular Structure and Dynamics* 10: 853-863 (1993)

Winfree, E.; Liu, F.; Wenzler, L. A.; Seeman, N. C., Design and self-assembly of two-dimensional DNA crystals, *Nature,* 394:539 (1998)

Zhu, L.; dos Santos, O.; Seeman, N. C.; Canary, J. W., Reaction of N3-benzoyl-3',5'-O-(di-tert-butylsilanediyl)uridine with hindered electrophiles: intermolecular N3 to 2'-O protecting group transfer, *Nucleosides, Nucleotides & Nucleic Acids,* 21:723-735 (2002)

What is claimed is:

1. A molecular knot structure formed from a ladder copolymer having two backbones as sides or legs of a ladder with links between the backbones serving as rungs of the ladder, wherein the ladder copolymer comprises the general formula (I)

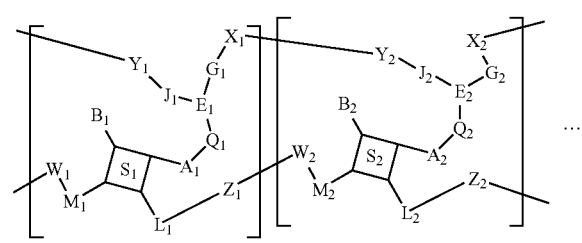

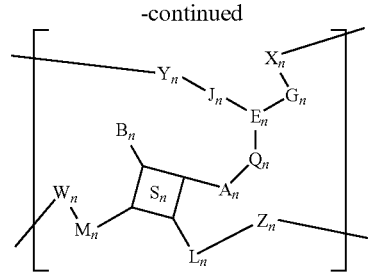

wherein:

$A_1$ to $A_n$ = a Group VI element selected from the group consisting of O, S, Se, and Te;

$G_1$ to $G_n$, $J_1$ to $J_n$, $L_1$ to $L_n$, $M_1$ to $M_n$, $Q_1$ to $Q_n$ = a linker group selected from the group consisting of $C_1$-$C_{18}$ branched or straight chain alkyl groups, $C_6$-$C_{24}$ substituted or unsubstituted aromatic and heteroaromatic groups having from 1-3 hetero atoms or halogen substitutions, —O—, —S—, carbonyl, carboxyl, —Si(R)$_2$—, and —OSi(R)$_2$O—;

$B_1$ to $B_n$=a nucleic acid base selected from the group consisting of uracil, thymine, adenine, guanine, cytosine, and modified pyrimidines and purines;

$E_1$ to $E_n$=a symmetric or asymmetric atom center selected from the group consisting of CR, N, NR+, phosphine, phosphine oxide, phosphate, phosphonate, phosphinate, phosphoramide, phosphonamide, and phosphinamide;

R=a terminal group selected from the group consisting of H, $C_1$-$C_{18}$ branched or straight chain alkyl groups, $C_6$-$C_{24}$ substituted or unsubstituted aromatic and heteroaromatic groups having from 1-3 hetero atoms or halogen substitutions;

$X_1$ to $X_n$, $Y_1$ to $Y_n$, $W_1$ to $W_n$ and $Z_1$ to $Z_n$ are each a functional group that when taken together as pairs X—Y and W—Z form amide, ester, phosphoester bonds, or alkene bonds; and $S_1$ to $S_n$=a ribose or a modified ribose.

2. The molecular knot structure of claim 1, wherein one of said backbones in the ladder copolymer is a polyamide backbone and the ladder copolymer comprises the general formula (II)

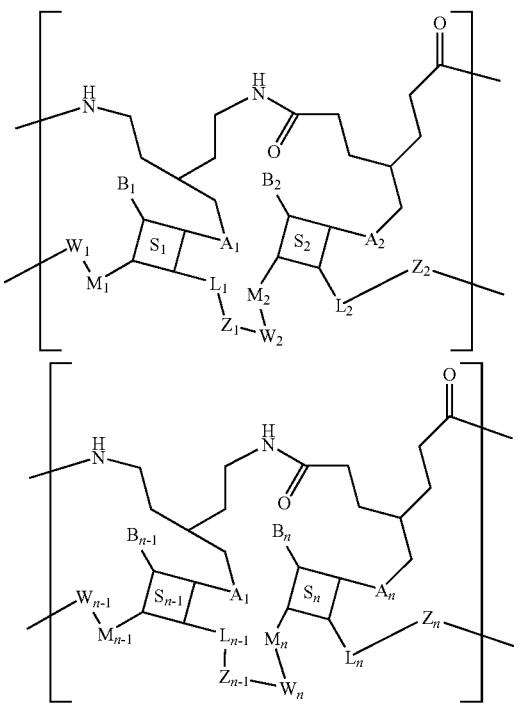

wherein:
$A_1$ to $A_n$=a Group VI element selected from the group consisting of O, S, Se, and Te; and
$L_1$ to $L_n$, $M_1$ to $M_n$=a linker group selected from the group consisting of $C_1$-$C_{18}$ branched or straight chain alkyl groups, $C_6$-$C_{24}$ substituted or unsubstituted aromatic and heteroaromatic groups having from 1-3 hetero atoms or halogen substitutions, —O—, —S—, carbonyl, carboxyl, —Si(R)$_2$—, and —OSi(R)$_2$O—;
$B_1$ to $B_n$=a nucleic acid base selected from the group consisting of uracil, thymine, adenine, guanine, cytosine, and modified pyrimidines and purines;

R=a terminal group selected from the group consisting of H, $C_1$-$C_{18}$ branched or straight chain alkyl groups, $C_6$-$C_{24}$ substituted or unsubstituted aromatic and heteroaromatic groups having from 1-3 hetero atoms or halogen substitutions;

$W_1$ to $W_n$ and $Z_1$ to $Z_n$ are each a functional group that when taken together as a pair form amide, ester, phosphoester bonds, or alkene bonds; and $S_1$ to $S_n$=a ribose or a modified ribose.

3. The molecular knot structure of claim 2, wherein, in the ladder copolymer, each of the 1-3 heteroatoms is independently selected from the group consisting of N, S and O.

4. The molecular knot structure of claim 1, wherein one of said backbones of the ladder copolymer is a nucleic acid backbone and the ladder copolymer comprises the general formula (III)

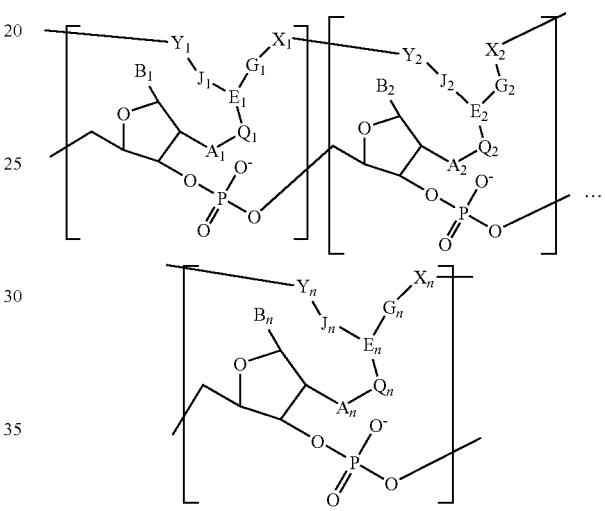

wherein:
$A_1$ to $A_n$=a Group VI element selected from the group consisting of O, S, Se, and Te;
$G_1$ to $G_n$, $J_1$ to $J_n$, $Q_1$ to $Q_n$=a linker group selected from the group consisting of $C_1$-$C_{18}$ branched or straight chain alkyl groups, $C_6$-$C_{24}$ substituted or unsubstituted aromatic and heteroaromatic groups having from 1-3 hetero atoms or halogen substitutions, —O—, —S—, carbonyl, carboxyl, —Si(R)$_2$—, and —OSi(R)$_2$O—;

$B_1$ to $B_n$=a nucleic acid base selected from the group consisting of uracil, thymine, adenine, guanine, cytosine, and modified pyrimidines and purines;

$E_1$ to $E_n$=a symmetric or asymmetric atom center selected from the group consisting of CR, N, NR+, phosphine, phosphine oxide, phosphate, phosphonate, phosphinate, phosphoramide, phosphonamide, and phosphinamide;

R=a terminal group selected from the group consisting of H, $C_1$-$C_{18}$ branched or straight chain alkyl groups, $C_6$-$C_{24}$ substituted or unsubstituted aromatic and heteroaromatic groups having from 1-3 hetero atoms or halogen substitutions; and $X_1$ to $X_n$ and $Y_1$ to $Y_n$ are each a functional group that when taken together as a pair form amide, ester, phosphoester bonds, or alkene bonds.

5. The molecular knot structure of claim 4, wherein, in the ladder copolymer, each of the 1-3 heteroatoms is independently selected from the group consisting of N, S and O.

6. A modified molecular knot structure comprising the general formula (III)

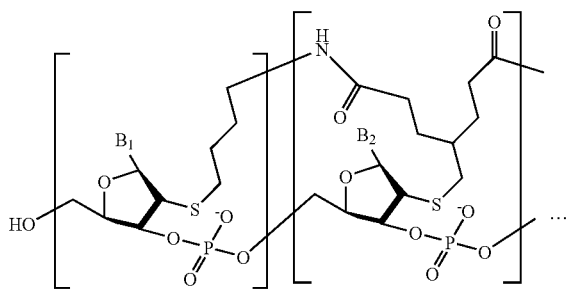

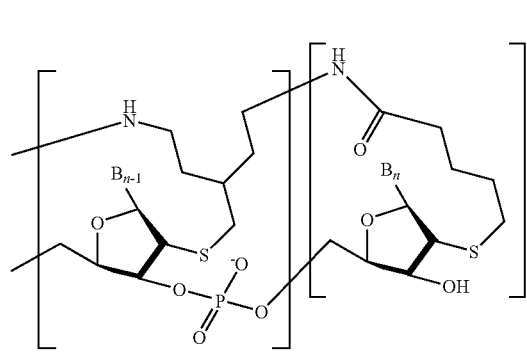

wherein:
- $A_1$ to $A_n$=a Group VI element selected from the group consisting of O, S, Se, and Te;
- $G_1$ to $G_n$, $J_1$ to $J_n$, $Q_1$ to $Q_n$=a linker group selected from the group consisting of $C_1$-$C_{18}$ branched or straight chain alkyl groups, $C_6$-$C_{24}$ substituted or unsubstituted aromatic and heteroaromatic groups having from 1-3 hetero atoms or halogen substitutions, —O—, —S—, carbonyl, carboxyl, —Si(R)$_2$—, and —OSi(R)$_2$O—;
- $B_1$ to $B_n$=a nucleic acid base selected from the group consisting of uracil, thymine, adenine, guanine, cytosine, and modified pyrimidines and purines;
- $E_1$ to $E_n$=a symmetric or asymmetric atom center selected from the group consisting of CR, N, NR+, phosphine, phosphine oxide, phosphate, phosphonate, phosphinate, phosphoramide, phosphonamide, and phosphinamide;
- R=a terminal group selected from the group consisting of H, $C_1$-$C_{18}$ branched or straight chain alkyl groups, $C_6$-$C_{24}$ substituted or unsubstituted aromatic and heteroaromatic groups having from 1-3 hetero atoms or halogen substitutions; and
- $X_1$ to $X_n$ and $Y_1$ to $Y_n$ are each a functional group that when taken together as a pair form amide, ester, phosphoester bonds, or alkene bonds, but in which the nucleic acid backbone is absent.

7. The molecular knot structure of claim 1, wherein said two backbones of the ladder copolymer are a polyamide backbone and a nucleic acid backbone.

8. The molecular knot structure of claim 7, wherein the ladder copolymer comprises the general formula (IV)

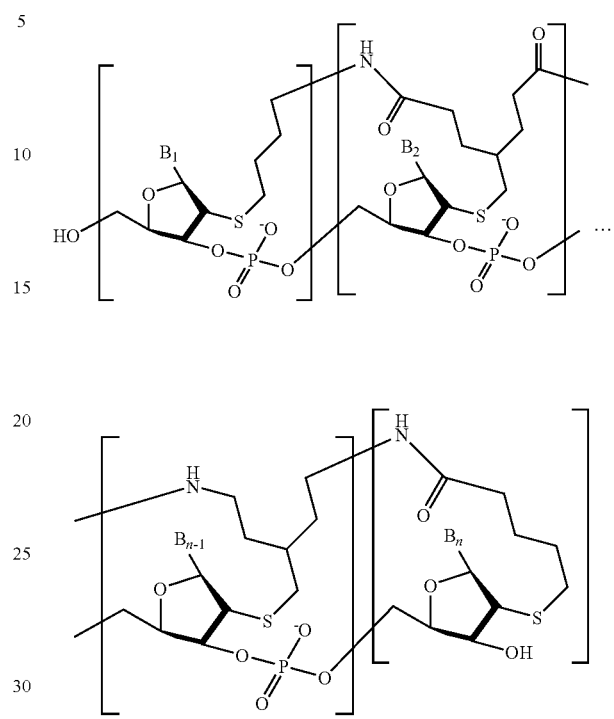

wherein B is a nucleic acid base selected from the group consisting of uracil, thymine, adenine, guanine, cytosine, and modified pyrimidines and purines.

9. The molecular knot structure of claim 1, wherein, in the ladder copolymer, each of the 1-3 heteroatoms is independently selected from the group consisting of N, S and O.

10. A molecular chain mail, comprising a plurality of the molecular knot structure of claim 1 linked together to form a molecular chain mail.

11. The modified molecular knot structure of claim 6, which is a nylon molecular knot structure.

12. A nylon chain mail, comprising a plurality of the nylon molecular knot structure of claim 11 linked together to form a nylon chain mail.

13. A molecular chain mail, comprising a plurality of the molecular knot structure of claim 6 linked together to form a molecular chain mail.

14. A method of preparing a modified molecular knot structure which comprises the general formula (III)

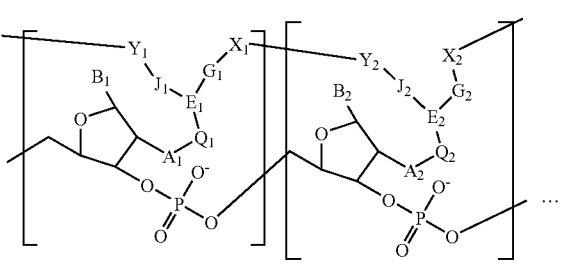

-continued

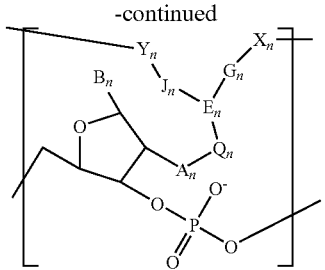

wherein:
- $A_1$ to $A_n$ = a Group VI element selected from the group consisting of O, S, Se, and Te;
- $G_1$ to $G_n$, $J_1$ to $J_n$, $Q_1$ to $Q_n$ = a linker group selected from the group consisting of $C_1$-$C_{18}$ branched or straight chain alkyl groups, $C_6$-$C_{24}$ substituted or unsubstituted aromatic and heteroaromatic groups having from 1-3 hetero atoms or halogen substitutions, —O—, —S—, carbonyl, carboxyl, —Si(R)$_2$—, and —OSi(R)$_2$O—;
- $B_1$ to $B_n$ = a nucleic acid base selected from the group consisting of uracil, thymine, adenine, guanine, cytosine, and modified pyrimidines and purines;
- $E_1$ to $E_n$ = a symmetric or asymmetric atom center selected from the group consisting of CR, N, NR+, phosphine, phosphine oxide, phosphate, phosphonate, phosphinate, phosphoramide, phosphonamide, and phosphinamide;
- R = a terminal group selected from the group consisting of H, $C_1$-$C_{18}$ branched or straight chain alkyl groups, $C_6$-$C_{24}$ substituted or unsubstituted aromatic and heteroaromatic groups having from 1-3 hetero atoms or halogen substitutions; and
- $X_1$ to $X_n$ and $Y_1$ to $Y_n$ are each a functional group that when taken together as a pair form amide, ester, phosphoester bonds, or alkene bonds, but in which the nucleic acid backbone is absent, the method comprising removing the nucleic acid backbone and leaving the other backbone as a polymer in retention of the knot structure.

15. The method of claim 14, wherein the modified molecular knot structure is a nylon molecular knot structure.

* * * * *